(12) United States Patent
Riles et al.

(10) Patent No.: US 8,608,703 B2
(45) Date of Patent: Dec. 17, 2013

(54) INFUSION FLOW GUIDEWIRE SYSTEM

(75) Inventors: John C. Riles, Minneapolis, MN (US);
Douglas J. Ball, Coon Rapids, MN (US); Michael J. Bonnette, Minneapolis, MN (US); Eric J. Thor, Arden Hills, MN (US); John L. Teschendorf, Lino Lakes, MN (US); Hieu V. Le, Brooklyn Park, MN (US)

(73) Assignee: Medrad, Inc., Indianola, PA (US)

( * ) Notice: Subject to any disclaimer, the term of this patent is extended or adjusted under 35 U.S.C. 154(b) by 1279 days.

(21) Appl. No.: 11/980,164

(22) Filed: Oct. 30, 2007

(65) Prior Publication Data
US 2008/0312671 A1    Dec. 18, 2008

Related U.S. Application Data

(60) Provisional application No. 60/934,281, filed on Jun. 12, 2007.

(51) Int. Cl.
*A61M 5/178*    (2006.01)
*A61M 25/00*    (2006.01)
*A61B 17/22*    (2006.01)
*A61D 1/02*     (2006.01)

(52) U.S. Cl.
USPC ............ 604/167.06; 604/164.13; 604/170.02; 604/524; 606/159

(58) Field of Classification Search
USPC .................. 604/158, 164.02, 164.07, 164.11, 604/164.13, 165.01–165.04, 167.01, 604/170.01, 170.02, 523, 524; 606/159
See application file for complete search history.

(56) References Cited

U.S. PATENT DOCUMENTS

| | | |
|---|---|---|
| 1,436,707 A | 11/1922 | Gaschke |
| 3,773,290 A | 11/1973 | Mowery |
| 4,039,266 A | 8/1977 | O'Connell |
| 4,122,556 A | 10/1978 | Poler |
| 4,166,807 A | 9/1979 | Komatsu et al. |
| 4,332,254 A | 6/1982 | Lundquist |
| 4,467,003 A | 8/1984 | Pallaroni et al. |
| 4,573,470 A | 3/1986 | Samson et al. |
| 4,573,966 A | 3/1986 | Weikl et al. |
| 4,636,195 A | 1/1987 | Wolinsky |

(Continued)

FOREIGN PATENT DOCUMENTS

| | | |
|---|---|---|
| EP | 0254885 | 2/1988 |
| EP | 0313836 | 3/1989 |

(Continued)

OTHER PUBLICATIONS

IB Report on Patentability mailed Dec. 30, 2009 in corresponding International Patent Application PCT/US08/66646.

(Continued)

*Primary Examiner* — Nathan R Price
(74) *Attorney, Agent, or Firm* — David Schramm

(57) ABSTRACT

An infusion flow guidewire system and method of use. The infusion flow guidewire system includes a delivery sheath and an infusion flow guidewire. The minimal cross section flexible infusion flow guidewire includes a flexible tip having a closed distal end, a coil, a core wire and at least one distally located jet orifice for infusion of fibrinolytics and for introduction of high pressure fluids for maceration and rearwardly directed flow of thrombus debris located in tortuous small sized vessels. Apparatus, some of which is removably attachable, is provided for grasping members of the invention for rotational torqueing and for longitudinal actuation along and within the vasculature.

28 Claims, 16 Drawing Sheets

(56) References Cited

U.S. PATENT DOCUMENTS

| | | |
|---|---|---|
| 4,646,719 A | 3/1987 | Neuman et al. |
| 4,651,738 A | 3/1987 | Demer et al. |
| 4,653,539 A | 3/1987 | Bell |
| 4,710,075 A | 12/1987 | Davison |
| 4,710,171 A | 12/1987 | Rosenberg |
| 4,733,652 A | 3/1988 | Kantrowitz et al. |
| 4,758,223 A | 7/1988 | Rydell |
| 4,787,794 A | 11/1988 | Guthrie |
| 4,832,023 A | 5/1989 | Murphy-Chutorian et al. |
| 4,838,268 A | 6/1989 | Keith et al. |
| 4,865,587 A | 9/1989 | Walling |
| 4,976,689 A | 12/1990 | Buchbinder et al. |
| 4,992,010 A | 2/1991 | Fischer |
| 5,014,494 A | 5/1991 | George |
| 5,045,061 A | 9/1991 | Seifert et al. |
| 5,059,176 A | 10/1991 | Winters |
| 5,059,178 A | 10/1991 | Ya |
| 5,085,635 A | 2/1992 | Cragg |
| 5,106,363 A | 4/1992 | Nobuyoshi |
| 5,135,482 A | 8/1992 | Neracher |
| 5,147,164 A | 9/1992 | Fraver |
| 5,167,239 A | 12/1992 | Cohen et al. |
| 5,171,221 A | 12/1992 | Samson |
| 5,176,692 A | 1/1993 | Wilk et al. |
| 5,178,158 A | 1/1993 | de Toledo |
| 5,184,627 A | 2/1993 | de Toledo |
| 5,195,955 A | 3/1993 | Don Michael |
| 5,196,245 A | 3/1993 | DeRudder et al. |
| 5,207,656 A | 5/1993 | Kranys |
| 5,209,727 A | 5/1993 | Radisch, Jr. et al. |
| 5,211,636 A | 5/1993 | Mische |
| 5,217,438 A | 6/1993 | Davis |
| 5,250,034 A | 10/1993 | Appling et al. |
| 5,320,604 A | 6/1994 | Walker et al. |
| 5,322,508 A | 6/1994 | Viera |
| 5,324,260 A | 6/1994 | O'Neill et al. |
| 5,328,472 A | 7/1994 | Steinke et al. |
| 5,334,153 A | 8/1994 | McIntyre et al. |
| 5,368,034 A | 11/1994 | Isner |
| 5,378,236 A | 1/1995 | Seifert |
| 5,380,284 A | 1/1995 | Don Michael |
| 5,399,658 A | 3/1995 | Archey et al. |
| 5,410,797 A | 5/1995 | Steinke et al. |
| 5,413,581 A | 5/1995 | Goy |
| 5,474,194 A | 12/1995 | Heilman et al. |
| 5,476,450 A | 12/1995 | Ruggio |
| 5,505,699 A | 4/1996 | Forman et al. |
| 5,514,109 A | 5/1996 | Mollenauer et al. |
| 5,520,645 A | 5/1996 | Imran et al. |
| 5,549,556 A | 8/1996 | Ndondo-Lay et al. |
| 5,549,557 A | 8/1996 | Steinke et al. |
| 5,554,114 A | 9/1996 | Wallace et al. |
| 5,583,047 A | 12/1996 | Blinka et al. |
| 5,584,843 A | 12/1996 | Wulfman et al. |
| 5,688,234 A | 11/1997 | Frisbie |
| 5,713,917 A | 2/1998 | Leonhardt et al. |
| 5,775,327 A | 7/1998 | Randolph et al. |
| 5,776,100 A | 7/1998 | Forman |
| 5,779,688 A | 7/1998 | Imran et al. |
| 5,779,721 A | 7/1998 | Nash |
| 5,792,179 A | 8/1998 | Sideris |
| 5,794,325 A | 8/1998 | Fallandy |
| 5,795,325 A | 8/1998 | Valley et al. |
| 5,807,330 A | 9/1998 | Teitelbaum |
| 5,810,871 A | 9/1998 | Tuckey et al. |
| 5,827,324 A | 10/1998 | Cassell et al. |
| 5,833,644 A | 11/1998 | Zadno-Azizi et al. |
| 5,833,650 A | 11/1998 | Imran |
| 5,843,022 A | 12/1998 | Willard et al. |
| 5,865,721 A | 2/1999 | Andrews et al. |
| 5,879,361 A | 3/1999 | Nash |
| 5,881,534 A | 3/1999 | Ahlqvist et al. |
| 5,908,405 A | 6/1999 | Imran et al. |
| 5,925,016 A | 7/1999 | Chornenky et al. |
| 5,938,672 A | 8/1999 | Nash |
| 5,957,901 A | 9/1999 | Mottola et al. |
| 5,961,510 A | 10/1999 | Fugoso et al. |
| 5,968,017 A | 10/1999 | Lampropoulos et al. |
| 5,997,558 A | 12/1999 | Nash |
| 6,021,340 A | 2/2000 | Randolph et al. |
| 6,022,336 A | 2/2000 | Zadno-Azizi et al. |
| 6,027,461 A | 2/2000 | Walker et al. |
| 6,036,715 A | 3/2000 | Yock |
| 6,050,972 A | 4/2000 | Zadno-Azizi et al. |
| 6,071,285 A | 6/2000 | Lashinski et al. |
| 6,080,170 A | 6/2000 | Nash et al. |
| 6,123,698 A | 9/2000 | Spears et al. |
| 6,135,991 A | 10/2000 | Muni et al. |
| 6,146,372 A | 11/2000 | Leschinsky et al. |
| 6,161,695 A | 12/2000 | Nicolais |
| 6,166,116 A | 12/2000 | Sleeckx |
| 6,171,328 B1 | 1/2001 | Addis |
| 6,174,316 B1 | 1/2001 | Tuckey et al. |
| 6,176,844 B1 | 1/2001 | Lee |
| 6,179,816 B1 | 1/2001 | Mottola et al. |
| 6,183,420 B1 | 2/2001 | Douk et al. |
| 6,190,354 B1 | 2/2001 | Sell et al. |
| 6,203,561 B1 | 3/2001 | Ramee et al. |
| 6,217,567 B1 | 4/2001 | Zadno-Azizi et al. |
| 6,224,570 B1 | 5/2001 | Le et al. |
| 6,231,588 B1 | 5/2001 | Zadno-Azizi |
| 6,241,706 B1 | 6/2001 | Leschinsky et al. |
| 6,241,744 B1 | 6/2001 | Imran et al. |
| 6,245,008 B1 | 6/2001 | Leschinsky et al. |
| 6,245,089 B1 | 6/2001 | Daniel et al. |
| 6,251,093 B1 | 6/2001 | Valley et al. |
| 6,273,880 B1 | 8/2001 | Berg et al. |
| 6,355,016 B1 | 3/2002 | Bagaoisan et al. |
| 6,387,071 B1 | 5/2002 | Constantz |
| 6,475,185 B1 | 11/2002 | Rauker et al. |
| 6,485,657 B1 | 11/2002 | Funakoshi et al. |
| 6,488,671 B1 | 12/2002 | Constantz et al. |
| 6,494,314 B1 | 12/2002 | Lamborne et al. |
| 6,517,518 B2 | 2/2003 | Nash et al. |
| 6,524,323 B1 | 2/2003 | Nash et al. |
| 6,533,751 B2 | 3/2003 | Cragg et al. |
| 6,533,763 B1 | 3/2003 | Schneiter |
| 6,533,767 B2 | 3/2003 | Johansson et al. |
| 6,544,276 B1 | 4/2003 | Azizi |
| 6,569,147 B1 | 5/2003 | Evans et al. |
| 6,569,151 B1 | 5/2003 | Nash et al. |
| 6,612,990 B1 | 9/2003 | Pruter |
| 6,652,546 B1 | 11/2003 | Nash et al. |
| 6,694,832 B1 | 2/2004 | Gleeson |
| 6,789,986 B2 | 9/2004 | Story, Jr. |
| 6,824,550 B1 | 11/2004 | Noriega et al. |
| 6,830,577 B2 | 12/2004 | Nash et al. |
| 6,843,797 B2 | 1/2005 | Nash et al. |
| 6,855,136 B2 | 2/2005 | Dorros et al. |
| 6,869,417 B1 | 3/2005 | Walters et al. |
| 6,872,192 B2 | 3/2005 | Nash et al. |
| 6,902,535 B2 | 6/2005 | Eberhart et al. |
| 6,905,505 B2 | 6/2005 | Nash et al. |
| 6,927,063 B2 | 8/2005 | Moreton et al. |
| 6,932,828 B2 | 8/2005 | Bonnette et al. |
| 6,936,056 B2 | 8/2005 | Nash et al. |
| 6,942,678 B2 | 9/2005 | Bonnette et al. |
| 6,962,707 B2 | 11/2005 | Schenk |
| 7,004,914 B2 | 2/2006 | Eberhart et al. |
| 7,048,696 B2 | 5/2006 | Eberhart et al. |
| 7,141,045 B2 | 11/2006 | Johansson et al. |
| 7,169,161 B2 | 1/2007 | Bonnette et al. |
| 7,219,799 B2 | 5/2007 | Bonnette et al. |
| 7,220,243 B2 | 5/2007 | Bonnette et al. |
| 7,226,425 B2 | 6/2007 | Eberhart et al. |
| 7,316,678 B2 | 1/2008 | Nash et al. |
| 7,334,681 B2 | 2/2008 | Bonnette et al. |
| 7,367,982 B2 | 5/2008 | Nash et al. |
| 7,374,560 B2 | 5/2008 | Ressemann et al. |
| 7,422,579 B2 | 9/2008 | Wahr et al. |
| 2001/0014821 A1 | 8/2001 | Juman et al. |
| 2001/0016704 A1 | 8/2001 | Zadno-Azizi et al. |
| 2002/0096521 A1 | 7/2002 | Cardarelli |
| 2002/0133117 A1 | 9/2002 | Zadno-Azizi et al. |

(56) References Cited

U.S. PATENT DOCUMENTS

| | | |
|---|---|---|
| 2003/0040705 A1 | 2/2003 | Dorros et al. |
| 2003/0088194 A1 | 5/2003 | Bonnette et al. |
| 2003/0088262 A1 | 5/2003 | Bonnette et al. |
| 2003/0088263 A1 | 5/2003 | Bonnette et al. |
| 2003/0208134 A1 | 11/2003 | Secrest et al. |
| 2004/0031721 A1 | 2/2004 | Mann |
| 2004/0039304 A1 | 2/2004 | Connors, III et al. |
| 2004/0039306 A1 | 2/2004 | Eberhart et al. |
| 2004/0039310 A1 | 2/2004 | Burkett |
| 2004/0050740 A1 | 3/2004 | Lewis |
| 2004/0059284 A1 | 3/2004 | Nash et al. |
| 2004/0097880 A1 | 5/2004 | Schur |
| 2004/0097995 A1 | 5/2004 | Nash et al. |
| 2004/0133185 A1 | 7/2004 | Nash et al. |
| 2004/0210164 A1 | 10/2004 | Eberhart et al. |
| 2005/0020998 A1 | 1/2005 | Bonnette et al. |
| 2005/0075647 A1 | 4/2005 | Walters et al. |
| 2005/0080357 A1 | 4/2005 | Eberhart et al. |
| 2005/0182437 A1 | 8/2005 | Bonnette et al. |
| 2005/0203425 A1 | 9/2005 | Langston |
| 2006/0074318 A1 | 4/2006 | Ahmed et al. |
| 2006/0129126 A1 | 6/2006 | Kaplitt et al. |
| 2006/0282015 A1 | 12/2006 | Eberhart et al. |
| 2007/0060878 A1 | 3/2007 | Bonnette |
| 2007/0060881 A1 | 3/2007 | Bonnette et al. |
| 2007/0073233 A1 | 3/2007 | Thor |
| 2007/0073271 A1 | 3/2007 | Brucker et al. |
| 2007/0106245 A1 | 5/2007 | McQueen et al. |
| 2007/0118072 A1 | 5/2007 | Nash |
| 2008/0027334 A1 | 1/2008 | Langston |
| 2008/0097294 A1 | 4/2008 | Prather et al. |

FOREIGN PATENT DOCUMENTS

| | | |
|---|---|---|
| WO | WO0224271 | 3/2002 |
| WO | WO02094364 | 11/2002 |
| WO | WO2004018032 | 3/2004 |
| WO | WO2004028592 | 4/2004 |
| WO | 2007053779 | 5/2007 |

OTHER PUBLICATIONS

Supplementary European Search Report issued Dec. 4, 2009 in corresponding EP 05772444.5.

U.S. Appl. No. 11/980,164, filed Oct. 30, 2007, "Infusion Flow Guidewire System", Riles.

International Search Report for related International Application PCT/US2008/066646, Dec. 9, 2008.

ProStream Infusion Wire Data Sheet, EV3, Sep. 2007.

MicroMewi Multiple Sidehole Infusion Catheter Data Sheet, Micro Therapeutics, Inc., Feb. 2005.

Supplemental European Search Report from related European Application, dated Sep. 26, 2011.

U.S. Appl. No. 11/702,990, filed Feb. 6, 2007, "Miniature Flexible Thrombectomy Catheter", Bonnette.

U.S. Appl. No. 11/702,995, filed Feb. 6, 2007, "Miniature Flexible Thrombectomy Catheter", Bonnette.

U.S. Appl. No. 11/294,006, filed Dec. 5, 2005, "Exhaust-Pressure-Operated Balloon Catheter System", Bonnette.

Angiojet Pump Set, Possis Medical, Inc. corporate website (www.possis.com), 2009.

CRW (Radionics) Disposable Depth Stops Product No. DS11, DS16, DS18, DS21, DS25 and DS30, CRW Catalog Product Sheet, 2006.

International Search Report of Related PCT Publication WO2008/157204 Dated Dec. 17, 2009.

International Preliminary Report on Patentability of Related PCT Publication WO2008/157204 Dated Dec. 9, 2008.

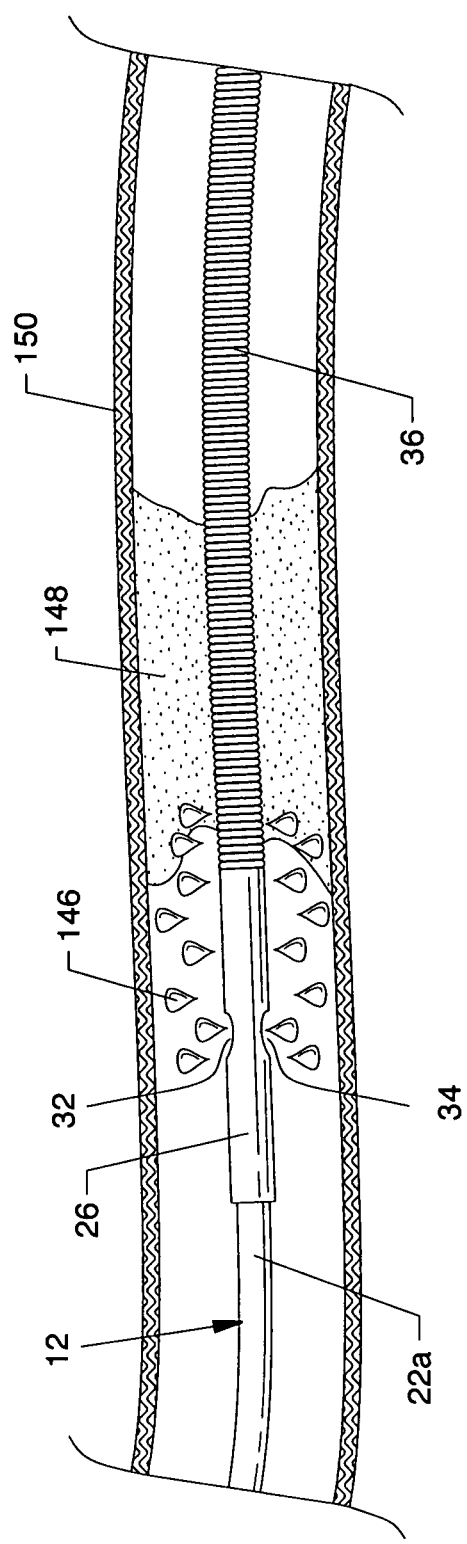

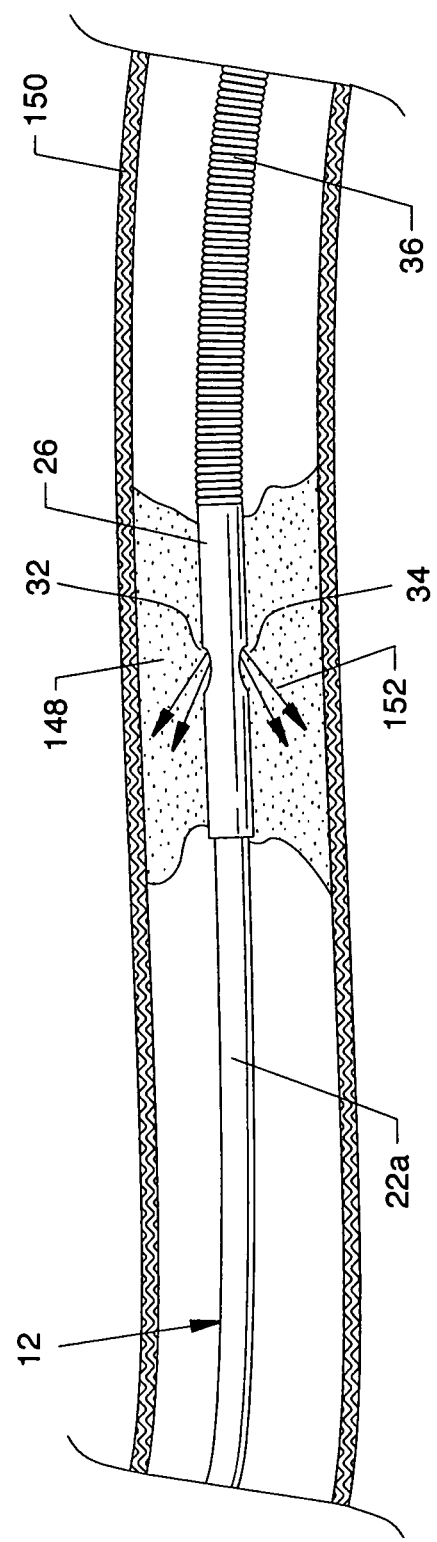

INFUSION FLOW GUIDEWIRE SYSTEM

CROSS REFERENCES TO RELATED APPLICATIONS

This patent application is related to patent application Ser. No. 11/702,990 filed Feb. 6, 2007, entitled "Miniature Flexible Thrombectomy Catheter," now Pat. No. 8,012,117; to patent application Ser. No. 11/702,995 filed Feb. 6, 2007, also entitled "Miniature Flexible Thrombectomy Catheter"; to patent application Ser. No. 11/237,558 filed Sep. 28, 2005, entitled "Thrombectomy Catheter Deployment System"; now Pat. No. 7,935,077; and to patent application Ser. No. 11/581,613 filed Oct. 16, 2006, entitled "Occlusive Guidewire System Having an Ergonomic Handheld Control Mechanism Prepackaged in a Pressurized Gaseous Environment and a Compatible Prepackaged Torqueable Kink-Resistant Guidewire with Distal Occlusive Balloon."

This application claims priority from the earlier filed U.S. Provisional Application No. 60/934,281 filed Jun. 12, 2007, entitled "Floppy Flow Wire", and is hereby incorporated into this application by reference as if fully set forth herein.

BACKGROUND OF THE INVENTION

1. Field of the Invention

The field of the present invention relates to mechanical thrombectomy and catheter directed thrombolysis and for use in neurologic arteries where vessels are characterized by difficulty to deliver ablation devices thereinto due to the small size of the vessel and the tortuousity of the vessels. High efficacy of any thrombus or clot removing device is highly desirable when dealing with the removal of organized and difficult to remove materials which have been expelled from the left atrium or aorta. Furthermore, a guidewire-type catheter that is highly deliverable, such as by the use of a 0.014 inch guidewire such as provided by the present invention, can be utilized in the distal arteries of the coronary or peripheral arteries especially when such a catheter must be delivered through diseased vessel segments since it has a small crossing profile and is structurally suited for such a task.

2. Description of the Prior Art

Prior art devices such as thrombectomy catheters and closely related devices have been previously developed and designed to access and treat sites along the neurological anatomy. Such devices included catheters which were delivered within the vasculature in two parts. First, a microcatheter which is essentially a tube functioning as the effluent lumen of the thrombectomy catheter would be delivered to the treatment site over a guidewire. Then, a nitinol jet body with a guidewire tip on it was delivered inside the microcatheter to the treatment site. The jet body is the part of the thrombectomy catheter that delivers saline to the distal end of the catheter. The jet body has small jet orifices that are partly responsible for the high back pressures developed by the catheter. The jet orifices are positioned to direct high speed fluid jet streams within the catheter body. In previous neurological thrombectomy catheters, the jet body was designed to include a short skirt. When the jet body was activated by pumped saline, recovered pressures within the catheter assembly would expand the skirt such that the two parts became a unified single catheter assembly. The sequential exchange of devices meant that no guidewire was in place once the jet body was delivered. Hence, there was ample lumen for suitable exhaust flow and the catheter size could be kept smaller due to the absence of a guidewire. Generally, this two-part configuration for delivery to access and treat the site was difficult to accomplish. Some microcatheters would actually stretch while the jet body was advanced through the lumen, hence the jet body was never exposed to enable its activation. On occasions, the microcatheter would ovalize or otherwise distort in a tortuous anatomy, thus making it difficult to deliver the jet body through such a misshaped lumen. Furthermore, interventionists are never comfortable giving up their wire position and removing the guidewire in exchange for a jet body was regarded as a bit awkward and non-intuitive. Previous versions of neurologic thrombectomy catheters were often underpowered for the tough thrombus that was found in embolic stroke patients (organized thrombus from the left atrium). With any given AngioJet® style catheter design, there is a tradeoff between the thrombectomy power of the catheter and the vessel safety of that catheter design. The essence of the problem is that neurological arteries are highly fragile since they have very thin and unsupported vessel walls and the clot material adhering thereto is tough and organized.

Currently produced 3 Fr catheters are designed to be more easily deliverable to small distal vessels and they are envisioned to be an improvement over first generation products. The 3 Fr catheters have a transitioned sized hypotube assembly which is intended to achieve a level of deliverability far superior to the currently available 4 Fr catheters and, due to their smaller profile, will greatly enhance their deliverability. Nevertheless, the 3 Fr catheter will not achieve the level of deliverability of a 0.014 inch infusion flow guidewire as discussed in the present invention. The crossing profile of 1.07 Fr of the 0.014 inch infusion flow guidewire versus the 3 Fr catheter is of substantial benefit. Furthermore, a catheter that rides over a guidewire will interact with the guidewire creating a drag which will diminish the ultimate deliverability of the catheter device, whereas a 0.014 inch infusion flow guidewire of the present invention does not have this problem.

SUMMARY OF THE INVENTION

The general purpose of the present invention is to provide a highly deliverable infusion flow guidewire having a substantial thrombectomy/fibrinolytic infusion effectiveness.

According to one or more illustrations of the present invention, there is provided an infusion flow guidewire system that is preferably used with an external pressurized fluid supply, such as an AngioJet® pump set or other suitable device. The infusion flow guidewire system is comprised of major structures including: an infusion flow guidewire; a delivery sheath having a proximally located torque handle; and a torque device which can be removably attached to the proximal end of the infusion flow guidewire to facilitate the connection of the proximal end of the infusion flow guidewire to the distal end of an external pressurized fluid supply.

The infusion flow guidewire is comprised of components which transitionally provide for increasing flexibility along the length of the infusion flow guidewire where the most flexible region of the guidewire is at the distal end thereof. A major portion of the infusion flow guidewire is a hypotube of flexible nitinol material which is drawn down to a reduced diameter section near the distal end thereof providing one portion thereof with increased flexibility. The drawn-down distal end of the flexible hypotube, herein referred to as the drawn hypotube section, extends through a reinforcement collar and is secured therein by laser welds, soldering, welding or other suitable method, and distally extends further a short distance to terminate and secure within the proximal end of an even more flexible coil of platinum. The proximal round end of a flexible gold-plated core wire is located and secured within the distal end of the drawn hypotube section of the flexible hypotube. It is in coaxial alignment with the distal end of the drawn hypotube section of the flexible hypotube and with the proximal portion of the flexible coil of platinum. It is mutually secured by laser swages, soldering, welding or other suitable method. The proximal round section of the flexible gold-plated core wire extends partially in a distal direction along and within the flexible coil of platinum preferably tapering along a distal direction to continually reduce the cross section. The round tapered shape of the flexible gold-plated core wire transitions into an even more flexible flat shape to extend along the distal region of the flexible coil of platinum. A flexible tip having shapeable attributes is comprised of a distal tip weld and portions of both the flexible coil and the core wire distal to the flexible coil. One or more rearwardly directed jet orifices extend through the reinforcement collar and through the drawn hypotube section for rearwardly directed jet flow therefrom.

A coupling assembly is provided for rapid connection of the proximal end of the infusion flow guidewire to a high pressure supply device, such as the AngioJet® pump set or other suitable device. The delivery sheath, including a proximally located torque handle, is provided for fixing the position of the delivery sheath with respect to the infusion flow guidewire or for combined unitary maneuvering thereof, as required.

SIGNIFICANT ASPECTS AND FEATURES OF THE PRESENT INVENTION

One significant aspect and feature of the infusion flow guidewire system, the present invention, is the use of an infusion flow guidewire with a delivery sheath.

One significant aspect and feature of the infusion flow guidewire is the use of high velocity fluid jet streams for drug infusion.

One significant aspect and feature of the infusion flow guidewire is the use of high velocity fluid jet streams for tissue maceration.

One significant aspect and feature of the infusion flow guidewire is the use of high velocity fluid jet streams for moving debris in a preferred direction.

Yet another significant aspect and feature of the infusion flow guidewire is the use of nitinol tubing for the body of the infusion flow guidewire for the purpose of kink resistance.

Another significant aspect and feature of the present invention is the use of a laser swaging technique for attaching a gold-plated flexible stainless steel guidewire tip core wire to a nitinol hypotube.

Still another significant aspect and feature of the present invention is the use of a nitinol hypotube for the body of the infusion flow guidewire for the purpose of maximizing flow rate, i.e., minimizing flow resistance by maximizing ID.

Yet another significant aspect and feature of the present invention is the use of a nitinol hypotube for the body of the infusion flow guidewire for the purpose of minimizing complex joints between dissimilar metals.

A further significant aspect and feature of the present invention is a delivery sheath for support in delivering the infusion flow guidewire and to aid in giving the guidewire a 1:1 torque ratio which is preferred for guidewires.

A still further significant aspect and feature of the present invention is a flow guidewire performing substantially as a 0.014 inch outer diameter guidewire.

A still further significant aspect and feature of the present invention is the use and design of an easily detachable coupling assembly connecting an infusion flow guidewire to a high pressure supply line and a high pressure supply.

A still further significant aspect and feature of the present invention is the use of a coupling assembly using collet and O-ring assemblies to grasp or provide a seal about the proximal end of an infusion flow guidewire.

A still further significant aspect and feature of the present invention is the use of a coupling assembly to removably secure to and rotationally and/or longitudinally maneuver an infusion flow guidewire.

A still further significant aspect and feature of the present invention is the use of a torque handle using a collet to grasp an infusion flow guidewire.

A still further significant aspect and feature of the present invention is the use of the components of a torque handle to secure to and rotationally and/or longitudinally maneuver a hypotube and/or a delivery sheath either unitarily or singly.

A still further significant aspect and feature of the present invention is a 0.014 inch infusion flow guidewire driven by a pressure exceeding 0.10 kpsi with a delivered flow rate in excess of 3 cc/min.

A still further significant aspect and feature of the present invention is a fluid jet stream velocity for a 0.014 inch infusion flow guidewire between 0.1 and 100 m/s.

A still further significant aspect and feature of the present invention is a fluid jet stream velocity for a 0.014 inch infusion flow guidewire greater than 100 m/s.

A still further significant aspect and feature of the present invention is the use of fluid jet streams emanating from the infusion flow guidewire in any direction (i.e., 360 degrees from the axis of the wire), such as distally, proximally, perpendicularly or combined and diverse direction.

A still further significant aspect and feature of the present invention is use of one or more fluid jet streams.

A still further significant aspect and feature of the present invention is use of round jet orifices with diameters greater than 0.001 inch and less than the diameter of the wire, although the jet orifices could be noncircular or elongated in shape or in other geometrically configured shapes.

A still further significant aspect and feature of the present invention is that this high pressure high velocity jet technology could also be used for larger guidewires with a 0.018 inch diameter or a 0.035 inch diameter, or guidewires with less than 0.045 inch diameter.

A still further significant aspect and feature of the present invention is the use of a stainless steel guidewire extension with an irregularly shaped distal end or with a conical shaped distal end which is accommodated by the inner diameter of the hypotube to increase the length of an infusion flow guidewire rapid exchange wire to function as an exchange length wire for over-the-wire device use.

A still further significant aspect and feature of the present invention is the use of the infusion flow guidewire with the Thrombectomy Catheter Deployment System disclosed in patent application Ser. No. 11/237,558 (The AngioJet® Ultra Console) by the inventors.

Yet a further significant aspect and feature of the present invention is to use the present invention in combination with other devices, such as a regular AngioJet® catheter, simple syringe suction catheters, roller pump facilitated suction or in an exhaust-pressure-operated balloon catheter system (Proxy Cat) disclosed in patent application Ser. No. 11/294,006 by the inventors or with other devices.

Having thus briefly described embodiments of the present invention having mentioned some significant aspects and features of the present invention, it is the principal object of the present invention to provide an infusion flow guidewire system.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 13 shows the location of the jet orifices in close proximity to and proximal to the thrombus;

DETAILED DESCRIPTION OF THE PREFERRED EMBODIMENTS

Figure 1:
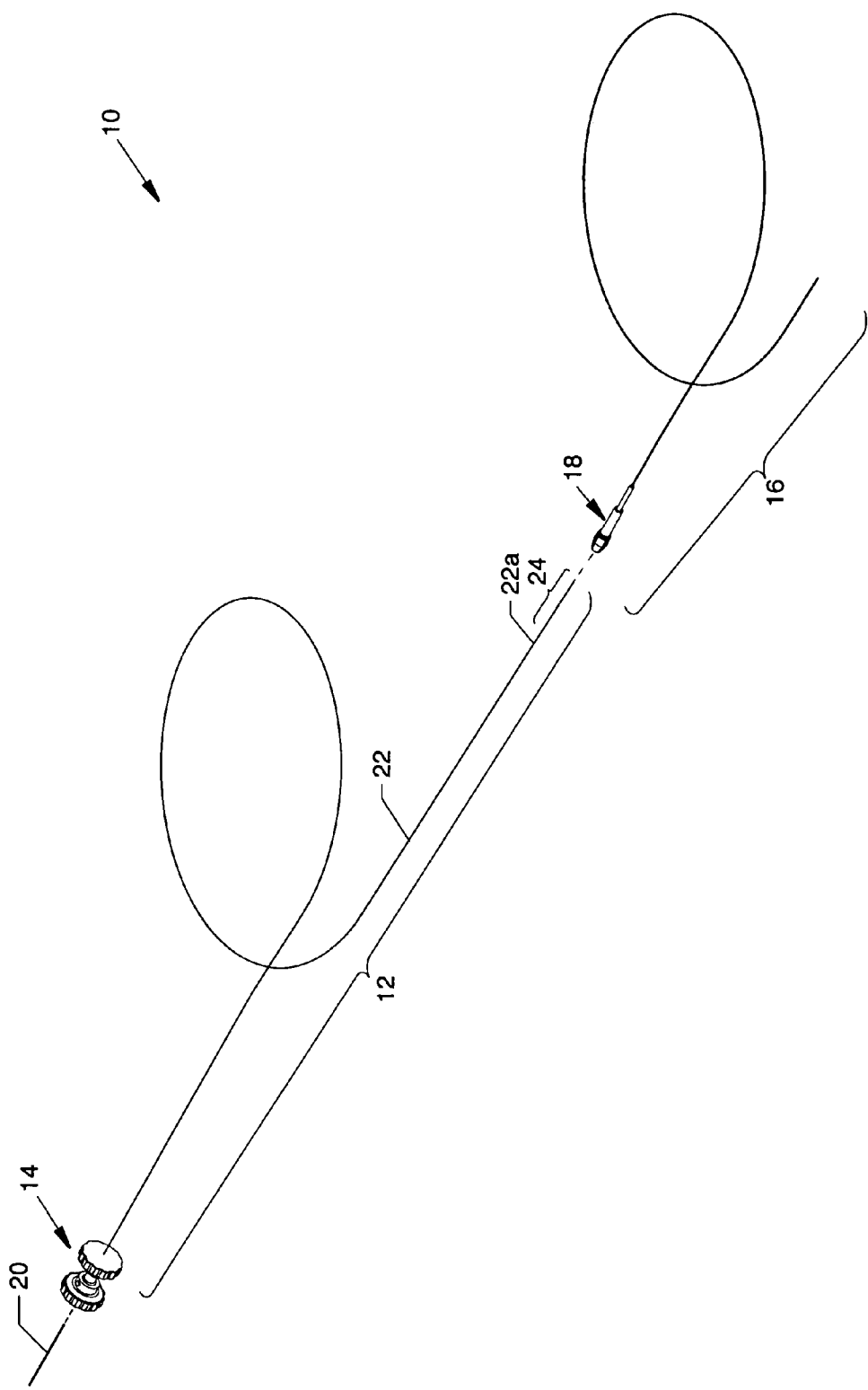
FIG. 1 is an isometric view of the infusion flow guidewire system where the major components of the system are shown separated, the present invention.
Figure 2:
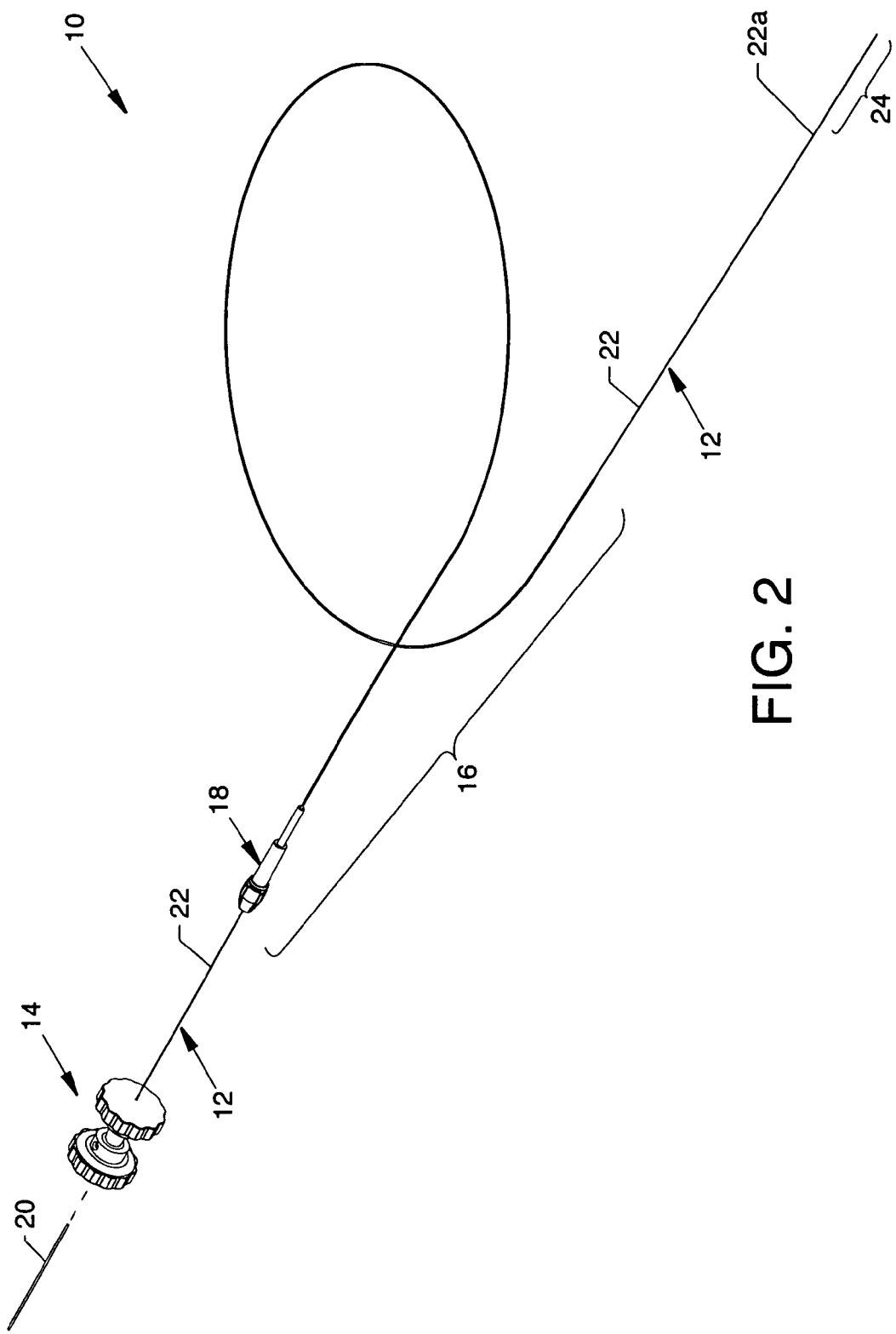
FIG. 2 is an isometric view of the infusion flow guidewire system in the engaged form.

FIG. 1 is an isometric view of the infusion flow guidewire system 10 wherein the major components are shown separated. FIG. 2 is an isometric view of the components of the infusion flow guidewire system 10 in the engaged form. Each figure illustrates readily visible components including: a flexible infusion flow guidewire 12 having a coupling assembly 14 removably attached at the proximal end thereof and a flexible delivery sheath 16 (also known as a guide catheter) of braided polyimide preferably having an outside diameter of 0.035 inch and an inner diameter of 0.017 inch. A proximally located torque handle 18 is shown attached to the proximal end of the delivery sheath 16. Special attention is paid to the connecting structure in the form of a high pressure supply line 20 which enables connection between an AngioJet® pump set (or another suitable device) and the infusion flow guidewire 12 where the high pressure supply line 20 does not exceed an infusion flow guidewire 12 having an outer diameter of 0.014 inch in order to enable the exchange of 0.014 inch compatible devices and does not impinge the inner diameter of 0.010 inch at the proximal end infusion flow guidewire 12 in order to provide for a suitable flow therethrough. For reference, the section of high pressure supply line 20 to which the invention can be attached is also shown in alignment with the proximal end of the coupling assembly 14.

The infusion flow guidewire 12 includes a hypotube 22 (a high pressure tube), preferably of flexible nitinol, at least one proximally directed jet orifice 32, 34 (FIG. 5), and a flexible tip 24, and other components described later in detail. Preferably, the greater portion of the hypotube 22 has an outer diameter of 0.014 inch and in inner diameter of 0.010 inch The hypotube 22 also includes a distally located drawn hypotube section 22a of reduced diameter for increased flexibility of the distal portion of the infusion flow guidewire 12. The multiple component shapeable and flexible tip 24, also shown in FIG. 3, which is located distally on the drawn hypotube section 22a, provides a flexibility greater than that of the drawn hypotube section 22a.

Figure 3:
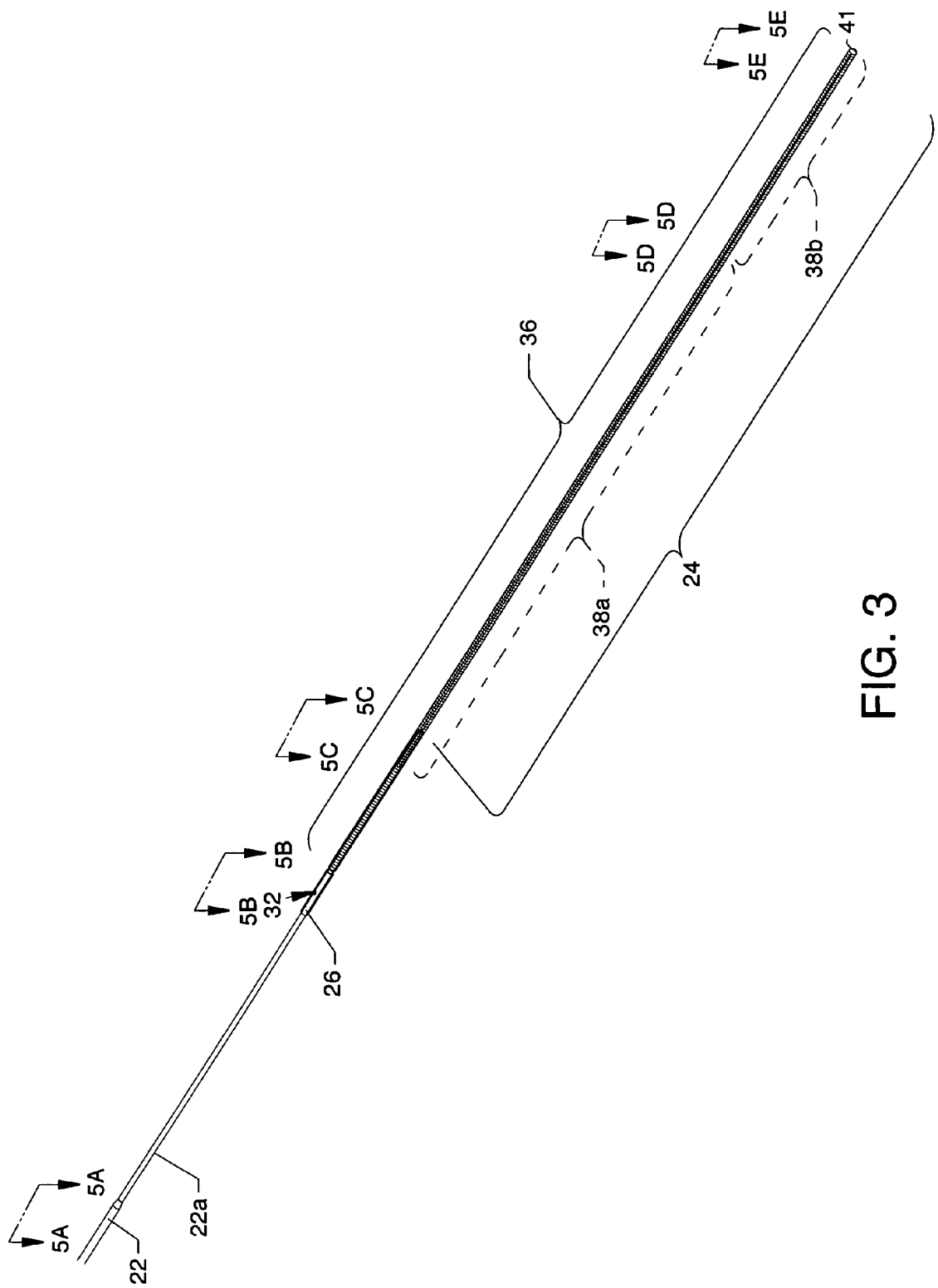
FIG. 3 is an assembled view of the drawn hypotube section and the flexible tip components of the guidewire system.
Figure 4:
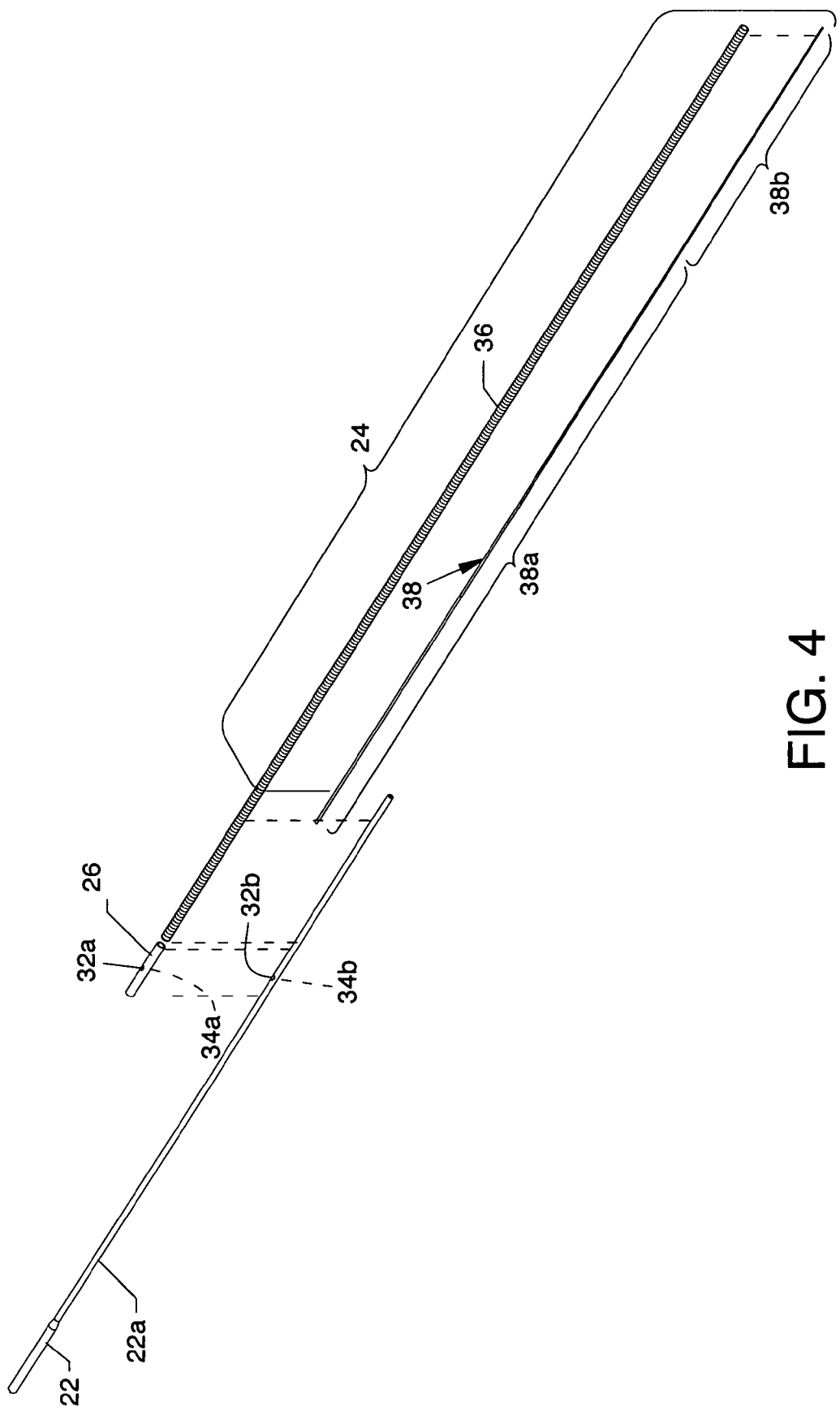
FIG. 4 is an exploded view of the components of FIG. 3.
Figure 5:
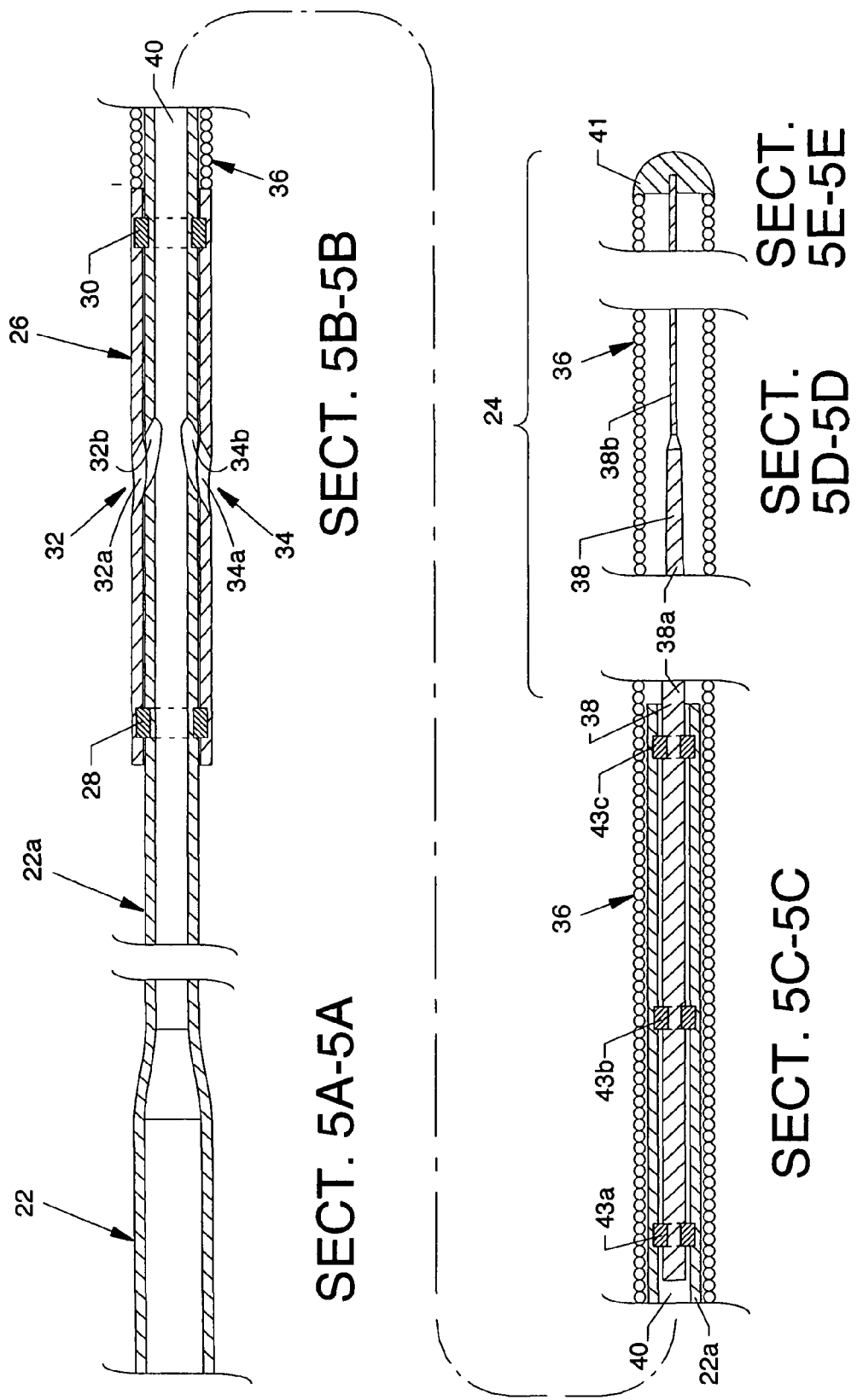
FIG. 5 shows views along section lines 5A-5A, 5B-5B, 5C-5C, 5D-5D and 5E-5E of FIG. 3.

With reference to FIGS. 3, 4 and 5, each figure shows different views in increasing detail exemplifying the generally overlapping and coaxial relationship of components of the flexible tip 24 to each other and to the drawn hypotube section 22a. The overlapping relationships and structure of such components are now described where FIG. 3 is an assembled view, FIG. 4 is an exploded view of the components of FIG. 3, and where FIG. 5 shows views along section lines 5A-5A, 5B-5B, 5C-5C, 5D-5D and 5E-5E of FIG. 3.

The complete length of a nitinol reinforcement collar 26 in the form of a tube (0.014 inch OD by 0.010 inch ID for purpose of example and illustration) is aligned over and about a distal region of the drawn hypotube section 22a at the distal end of the hypotube 22 and is secured thereto by laser welds 28 and 30 as shown in FIG. 5. As shown in section line 5b-5b of FIG. 5, a unitary rearwardly directed jet orifice 32 is provided by a hole 32a in the reinforcement collar 26 in close alignment with a hole 32b in the distal region of the drawn hypotube section 22a and, correspondingly, another unitary rearwardly directed jet orifice 34 is provided by a hole 34a in the reinforcement collar 26 in close alignment with a hole 34b in the distal region of the drawn hypotube section 22a. The reinforcement collar 26 provides a structural support along and about the drawn hypotube section 22a in the region of the jet orifices 32 and 34. The rearwardly directed jet orifices 32 and 34 are used to direct high pressure fluid jet streams proximally, as later described in detail. One or more such rearwardly directed jet orifices, such as jet orifices 32 and 34, may be formed by electrical discharge machining or by other suitable processes. Although symmetric rearwardly directed orifices 32 and 34 are shown, other symmetric or asymmetric jet orifice configurations can be used including one or more orifices which can be rearwardly, forwardly, perpendicularly directed in one or more directions or combinations of directions.

At the distal region of the infusion flow guidewire 12, the proximal end of a flexible coil 36 (preferably of, but not limited to, platinum) is aligned over and about the distal end of the drawn hypotube section 22a and can be soldered, welded or otherwise suitably secured thereto. The proximal terminus of the flexible coil 36 is aligned with the distal terminus end of the reinforcement collar 26 and can be soldered, welded, or otherwise suitably secured thereto.

A flexible core wire 38 of gold-plated steel consists of a core wire round section 38a with a contiguous core wire flat section 38b of the same material. The core wire 38 is attached to the distal end of the drawn hypotube section 22a and extends distally therefrom and is in coaxial alignment with the flexible coil 36 along the inner length thereof. More specifically, the proximal end of the core wire round section 38*a* is aligned within the lumen 40 of the drawn hypotube section 22*a*. At the distal end of the drawn hypotube section 22*a*, the core wire round section 38*a* is in direct coaxial alignment within the inner and distal portion of the drawn hypotube section 22*a* and in indirect coaxial alignment with the proximal portion of the flexible coil 36. The proximal end of the gold-plated core wire round section 38*a* is secured to the inner wall of the drawn hypotube section 22*a* by laser swages 43*a*, 43*b* and 43*c* by the process referred to in related patent application Ser. No. 11/702,990 filed Feb. 6, 2007, entitled "Miniature Flexible Thrombectomy Catheter," and to patent application Ser. No. 11/702,995 filed Feb. 6, 2007, also entitled "Miniature Flexible Thrombectomy Catheter," describing the process and use of laser swaging of gold-plated components to nitinol components. Such laser swaging of components, as described therein, provides for superior attachment and connection of the proximal end of the gold-plated core wire round section 38*a* to the drawn hypotube section 22*a* without degrading or weakening the swaged components. Preferably, the diameter of the core wire round section 38*a* is reduced in a distal direction transitioning to the flattened profile of the core wire flat section 38*b*. The core wire flat section 38*b* extends along the inner and distal portion of the flexible coil 36, thus providing an increased flexibility along the length of the flexible core wire 38. The distal terminus of the core wire flat section 38*b* is secured to the distal terminus of the flexible coil 36, such as by a weld 41.

Figure 6:
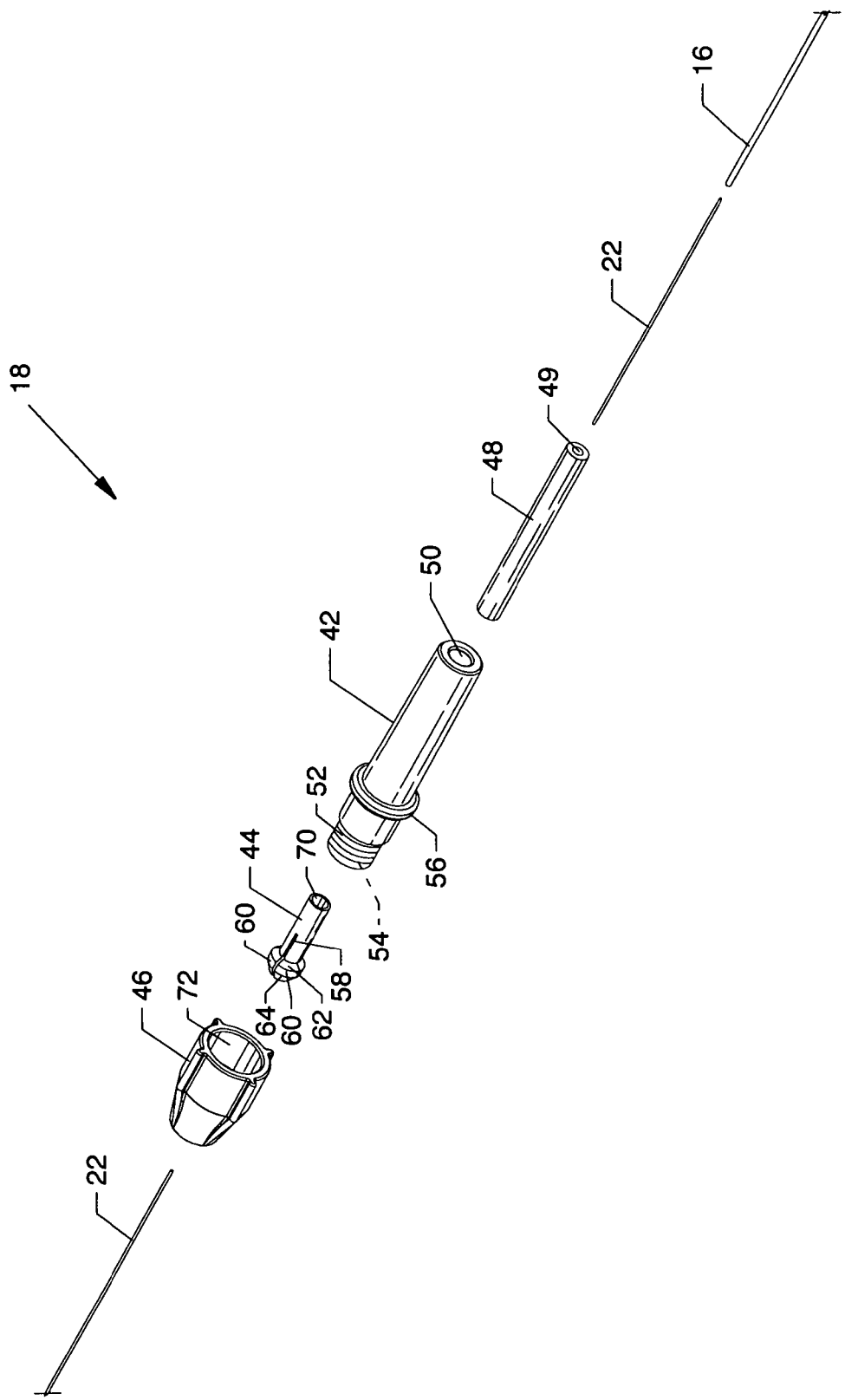
FIG. 6 is an exploded isometric view of a torque handle.
Figure 7:
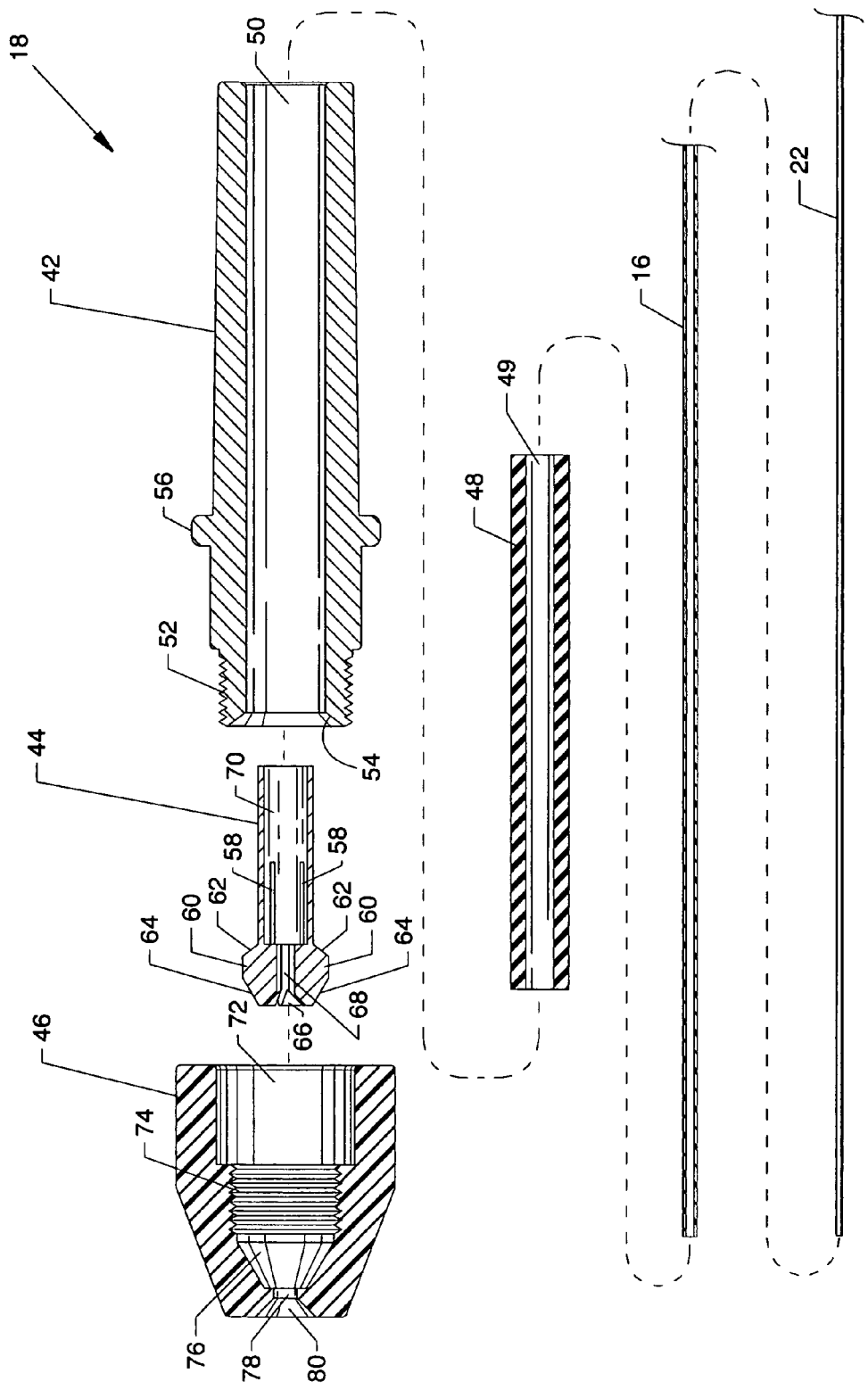
FIG. 7 is an exploded vertical cross section view of the components of FIG. 6.
Figure 8:
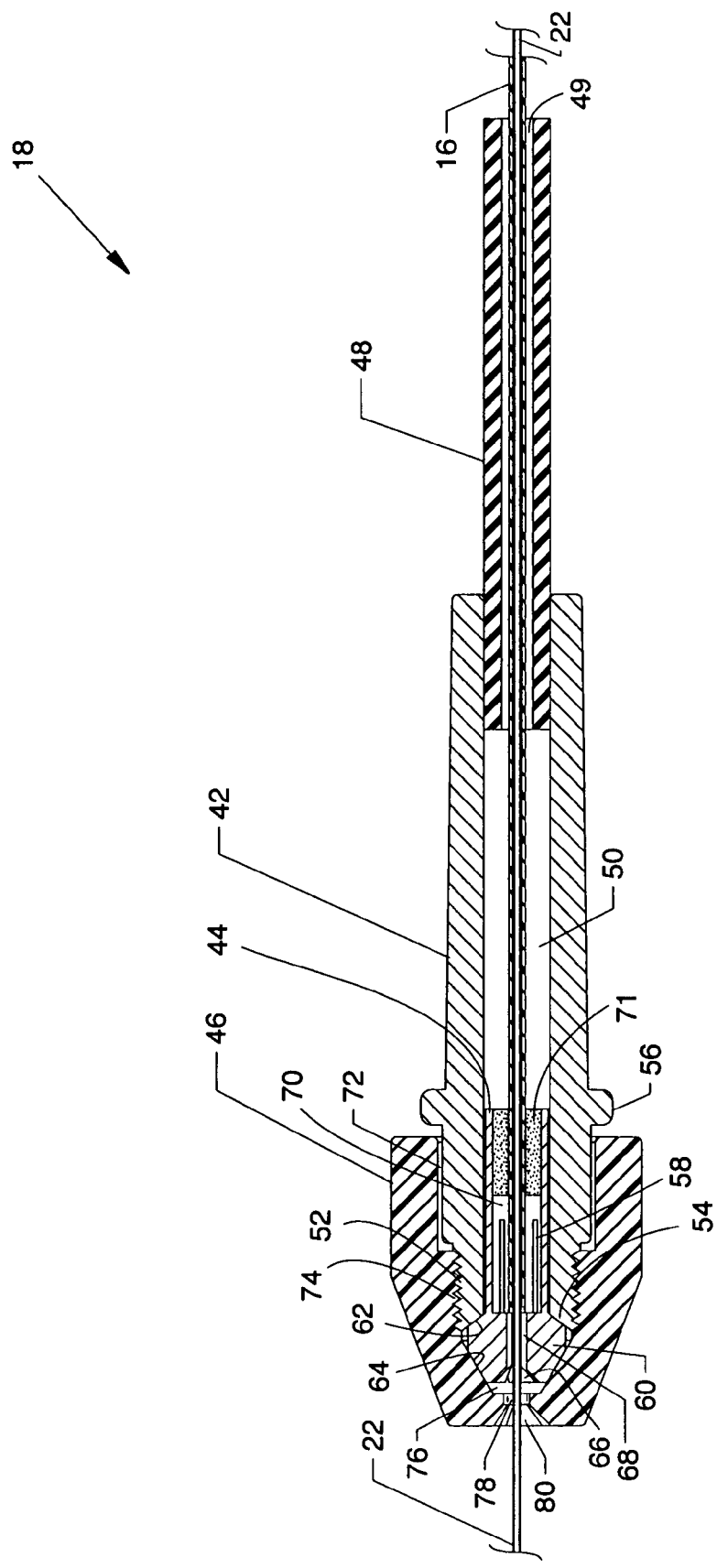
FIG. 8 is a view of the components shown in cross section in FIG. 7 arranged as an assembly.

With reference to FIGS. 6, 7 and 8, each figure shows the relationships of components of the torque handle 18 to each other, to the hypotube section 22 and to the delivery sheath 16. The relationships and the structure of such components are now described where FIG. 6 is an exploded isometric view of the torque handle, FIG. 7 is an exploded vertical cross section view of the components of FIG. 6, and FIG. 8 is a view of the components shown in cross section in FIG. 7 arranged as an assembly.

The torque handle 18 includes a torque body 42, a collet 44, a collet nut 46, and a strain relief 48 having a passage 49, the assembly of which provides for the coaxial accommodation of the delivery sheath 16 and the hypotube 22. The torque body 42 is generally cylindrical in shape and includes a centrally located bore 50, proximally located external threads 52, and a proximally located annular tapered actuating surface 54 located between the proximal end of the bore 50 and the proximal end of the threads 52. The centrally located bore 50 accommodates portions of one or more components including the hypotube 22, the delivery sheath 16, and one end of the strain relief 48 in coaxial fashion. An annular positioning ring 56 is also located about the exterior of the torque body 42.

The collet 44, as generally known in the art, includes at least a plurality of like spaced slots 58 extending longitudinally along a portion of such a collet 44 defining, in part, a plurality of like spaced flexible jaws 60, each having a distally located tapered and arcuate surface 62 for collective simultaneous forced interaction with the annular tapered actuating surface 54 of the torque body 42. Each of the like spaced flexible jaws 60 of the collet 44 has a proximally located tapered and arcuate surface 64 for collective simultaneous forced interaction with features of the collet nut 46, such features being later described in detail. Each of the like spaced flexible jaws 60 includes a centrally located tapered arcuate surface 66, preferably an inward taper, to accommodate the loading of the hypotube 22 from a proximal location. The tapered arcuate surfaces 66 of the collet 44 adjoin a passageway 68 located between the innermost portions of the flexible jaws 60 and which passageway 68 adjoins a larger bore 70. The passageway 68 accommodates the hypotube 22 in coaxial fashion and the bore 70 accommodates the hypotube 22 and the proximal end of the delivery sheath 16 in coaxial fashion. The proximal end of the delivery sheath 16 secures centrally within the bore 70 in alignment with the passageway 68, such as by adhesive 71 or other suitable method. The strain relief 48 secures in the bore 50 of the torque body 42.

The collet nut 46 includes a centrally located bore 72 aligned with internal threads 74 which accommodate the external threads 52 and the adjacent unthreaded proximal end of the torque body 42, respectively. An internal annular tapered surface 76 extends in a proximal direction from the internal threads 74. A passageway 78 adjoins the annular tapered surface 76. An outwardly opening annular tapered passageway 80 adjoins the passageway 78. The tapered wall of the annular tapered passageway 80 accommodates the insertion of the hypotube 22. In order to frictionally engage the hypotube 22, the wall of the annular tapered surface 76 maintains a forced intimate contact with the tapered and arcuate surfaces 64 of the collet 44 in order to flex and force the collet jaws 60 against the hypotube 22 in the passageway 68 in frictional engagement when the collet nut 46 and the torque body 42. Either the collet nut 46 or the torque body 42 is rotated with respect to each other to draw the torque body 42 and the collet nut 46 together about the collet 44. Thus, the torque handle 18 is engaged in frictional engagement with and about the hypotube 22 in order that a unitary longitudinal and/or torque movement of the infusion flow guidewire 12 and the delivery sheath 16 can be accomplished within the vasculature.

Independent movement of the infusion flow guidewire 12 or of the delivery sheath 16 with respect to each other or within the vasculature can be accomplished by loosening the collet nut 46 in order to release the frictional engagement of the torque handle 18 with the hypotube 22. Longitudinal and/or torque movement of the delivery sheath 16 can be accomplished by grasping and actuating the torque body 42. Longitudinal and/or torque movement of the infusion flow guidewire 12 can be accomplished without interference with the torque handle 18 by grasping and actuating the torque coupling assembly 14 which can be in frictional engagement with the proximal end of the hypotube 22, as later described in detail.

Figure 9:
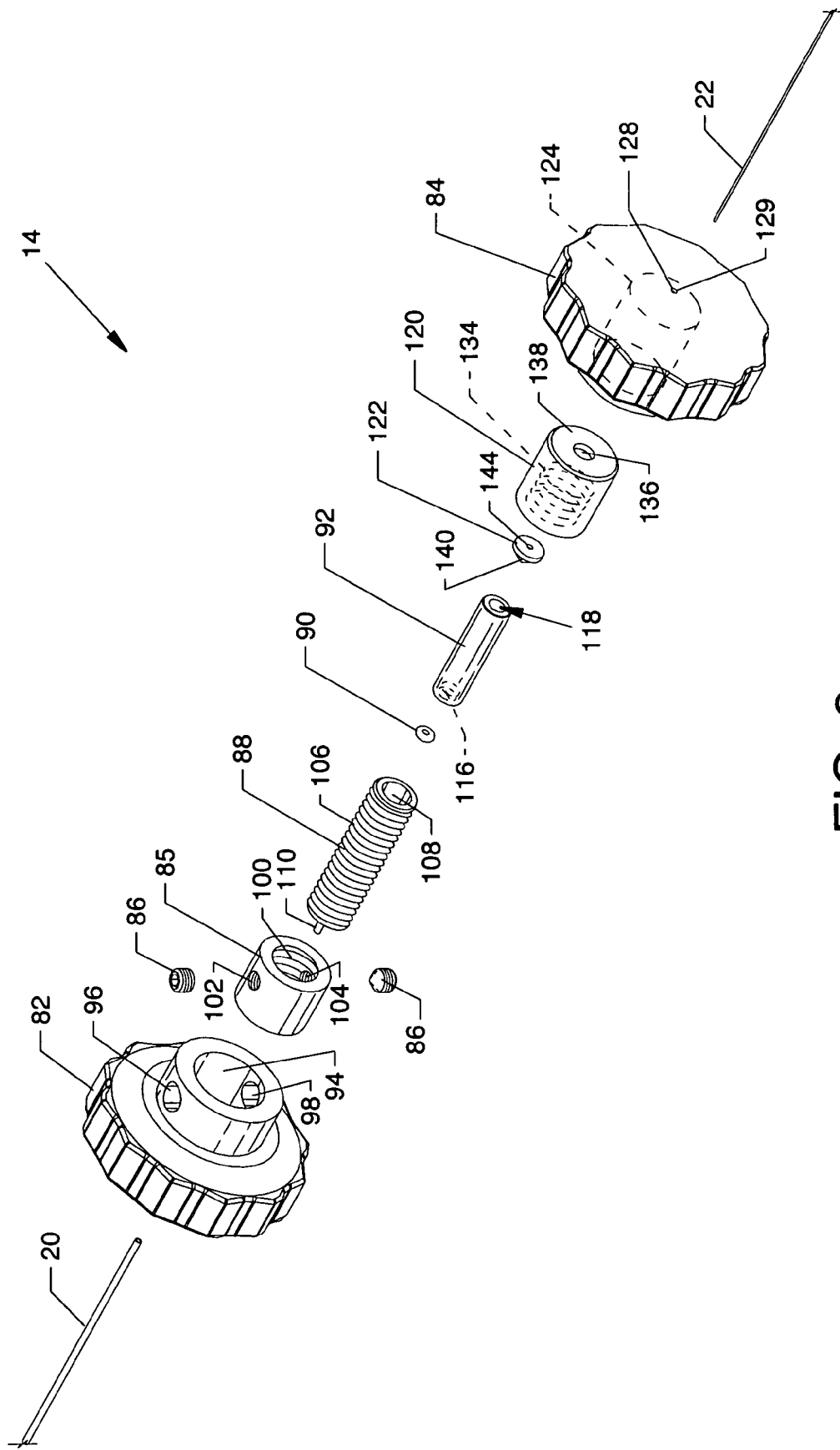
FIG. 9 is an exploded isometric view of a coupling assembly.
Figure 10:
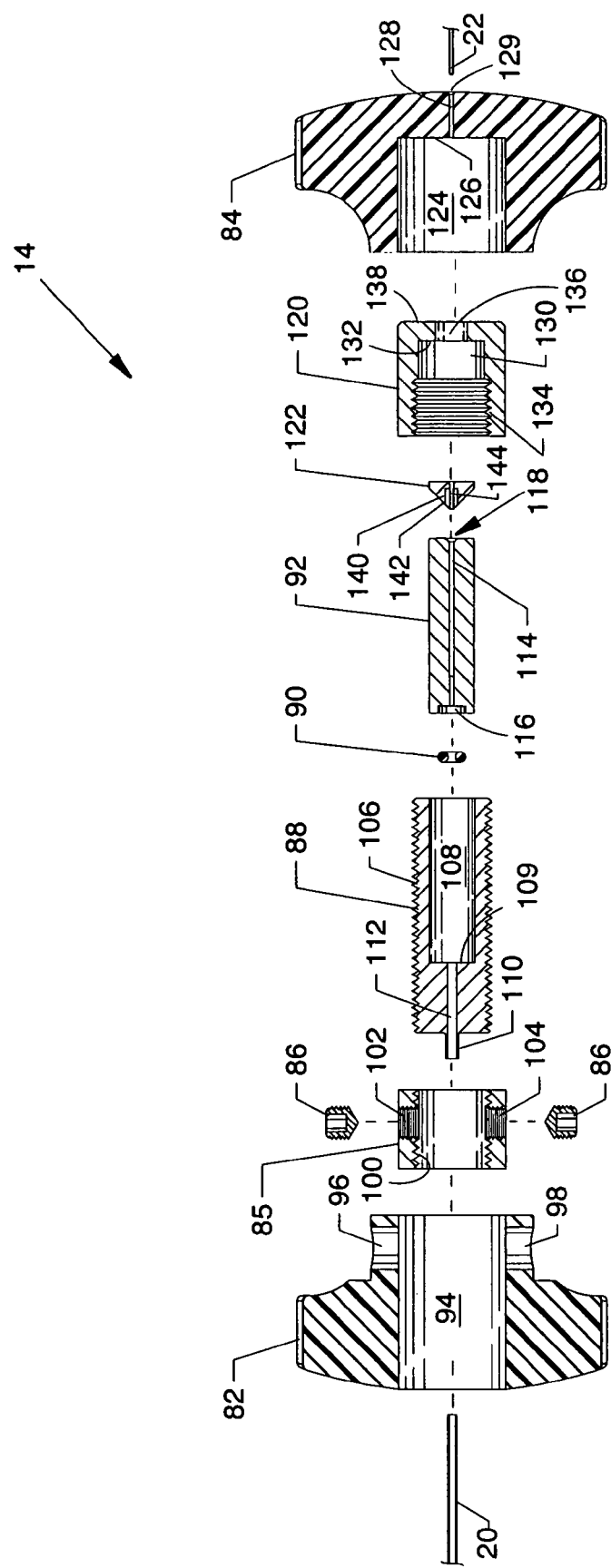
FIG. 10 is an exploded vertical cross section view of the components of FIG. 9.
Figure 11:
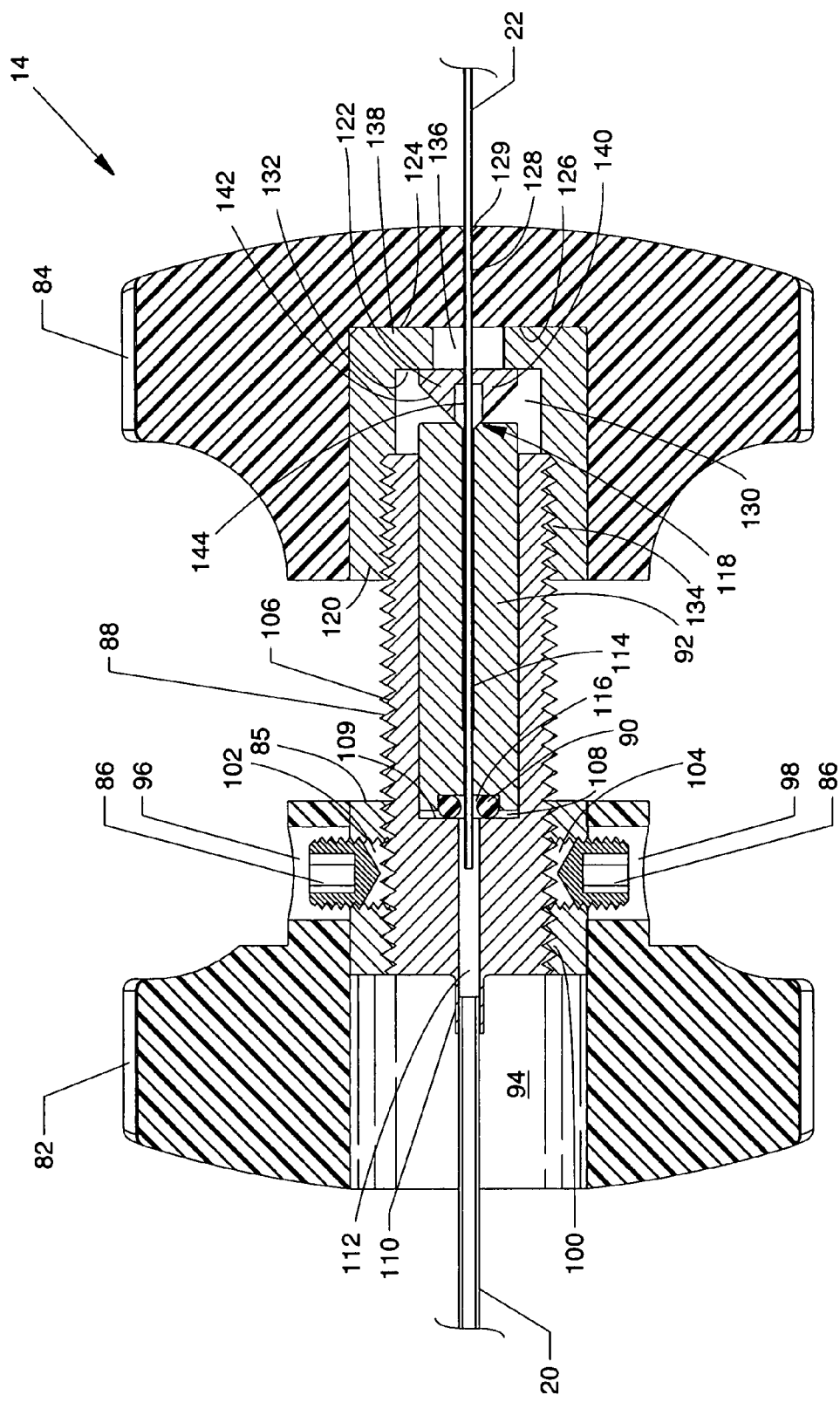
FIG. 11 is a view of the components shown in cross section in FIG. 10 arranged as an assembly.

With reference to FIGS. 9, 10 and 11, each figure shows different relationships of components of the coupling assembly 14 to each other, to the high pressure supply line 20 and to the hypotube section 22. Such relationships and the structure of the components are now described where FIG. 9 is an exploded isometric view of the torque coupling assembly 14, FIG. 10 is an exploded vertical cross section view of the components shown in FIG. 9, and FIG. 11 is a view of the components shown in cross section in FIG. 10 arranged as an assembly.

The coupling assembly 14, which is removably attached to the hypotube 22 of the infusion flow guidewire 12, is provided for rapid connection of the proximal end of the hypotube 22 of the infusion flow guidewire 12 to a high pressure supply device, such as the AngioJet® pump set or other suitable device. The AngioJet® pump set is described in detail in patent application Ser. No. 11/237,558 filed Sep. 28, 2005, entitled "Thrombectomy Catheter Deployment System". In particular, the coupling assembly 14 provides for communication and connection between the proximal end of the hypotube 22 to the distal end of the high pressure supply line 20 which is connected to a high pressure supply device. The coupling assembly 14 includes a proximal knob 82 which generally is stationary with reference to an opposing distal knob 84. The distal knob 84 is rotatable with reference to the proximal knob 82. The proximal knob 82 is indirectly connected to the distal end of the high pressure supply line 20, as later described in detail. The distal knob 84 is used for removable attachment of the proximal end of the hypotube 22 to provide communication of the hypotube 22 with the proximal end of the high pressure supply line 20, the latter being secured indirectly to the proximal knob 82.

A plurality of components, which components are substantially stationary, is connected to and associated with the generally stationary proximal knob 82 and include a threaded insert 85, set screws 86, a threaded body 88, an O-ring 90, and a compression fixture 92. The stationary proximal knob 82 includes a longitudinally oriented central bore 94 and opposed body holes 96 and 98 aligned perpendicular to and intersecting the bore 94 for accessing of the set screws 86. The threaded insert 85 is aligned in and is suitably secured within the central bore 94 of the proximal knob 82, such as by, but not limited to, the use of adhesives or frictional engagement. The threaded insert 85 includes internal threads 100 and threaded holes 102 and 104 aligned perpendicular to and intersecting the internal threads 100 in order to facilitate threaded engagement of the set screws 86 with the proximal end of the threaded body 88 to ensure secure fastening of the threaded body 88 within the internal threads 100 of the threaded insert 85. The threaded body 88 includes external threads 106 with the proximal portion of the threads 106 threadingly engaging the threads 100 of the threaded insert 85. The threaded body 88 also includes a partial bore 108 having an internal annular end surface 109, a centrally located proximally extending tubular flange 110, and a passageway 112 (FIG. 10), being part of the tubular flange 110 extending through the tubular flange 110 and connecting to the bore 108. The distal end of the high pressure supply line 20 is suitably secured to the tubular flange 110 within the proximal portion of the passageway 112 of the tubular flange 110, as shown in FIG. 11. The compression fixture 92 has a generally cylindrical shape and includes a passageway 114 extending along the longitudinal axis thereof. The compression fixture 92 terminates proximally at an annular recess 116 and distally at an annular tapered actuating surface 118. The annular recess 116 of the compression fixture 92 accommodates the O-ring 90. The compression fixture 92 aligns closely within the bore 108 of the threaded body 88 and is longitudinally positionable therewithin.

A plurality of components, which can be unitarily actuated in rotary fashion, is connected to and associated with the distal knob 84 including a threaded insert 120 and a tubular collet 122. The distal knob 84 includes a bore 124 terminating at an annular end surface 126 and a passageway 128 having a taper 129 extending from the annular end surface 126 through the distal wall of the distal knob 84 for accommodation of the hypotube 22. The threaded insert 120 includes a partial bore 130 terminating at one end by an annular end surface 132 and at the other end by adjacent threads 134. The threads 134 progressively engage the distal portion of the external threads 106 of the threaded body 88. A passageway 136 extends from the bore 130 through a distal wall 138 of the threaded insert 120. The tubular collet 122 includes a plurality of like spaced flexible jaws 140 each having a tapered and arcuate surface 142 surrounding a centrally located multiple radius passageway 144. The threaded insert 120 is suitably secured within the bore 124 of the distal knob 84, such as, but not limited to, by the use of adhesives or frictional engagement. The tubular collet 122 aligns to the annular end surface 132 of the threaded insert 120, whereby the passageway 144 of the tubular collet 122 and the passageway 136 of the threaded insert 120 are in coaxial alignment.

The coupling assembly 14, which is removably attached to the hypotube 22 of the infusion flow guidewire 12 and which is provided for rapid connection to the proximal end of the hypotube 22 of the infusion flow guidewire 12, uses previously described structure to effect suitable connection and coupling thereof and therewith. More specifically, the components of the coupling assembly 14 are assembled, as shown in FIG. 11, where the hypotube 22 is positioned, sealed and secured within the coupling assembly 14. The hypotube 22 is shown in coaxial direct alignment within the passageway 128 and taper 129 of the distal knob 84, the passageway 136 of the threaded insert 120, the passageway 144 of the tubular collet 122, the annular tapered actuating surface 118 of the compression fixture 92, the passageway 114 of the compression fixture 92, the center of the O-ring 90, and finally, within and in communication with the passageway 112 of the threaded body 88 resulting in a suitable communication with the high pressure supply line 20. As the distal knob 84 is rotated and advanced proximally along the threads 106 of the threaded body 88, the tube collet 122 is forcefully positioned against the annular tapered actuating surface 118 of the compression fixture 92, thereby urging and advancing the compression fixture 92 proximally. During such urging and advancement, sealing and securing of the hypotube 22 within the coupling assembly 14 are accomplished. Sealing is provided by the resultant advancement of the compression fixture 92 to cause the O-ring 90, which is located in the annular recess 116 of the compression fixture 92, to bear against the annular end surface 109 of the threaded body 88 to deform the O-ring 90 thereby effecting a seal about the hypotube 22, as well as perfecting a seal with the passageway 112 of the threaded body 88. A seal is also perfected between the bore 108 of the threaded body 88 and the passageway 112 of the threaded body 88. Securing of the hypotube 22 within the coupling assembly 14 is provided by the interaction of the advancing tapered and arcuate surfaces 142 of the tubular collet jaws 140 with the annular tapered actuating surface 118 of the compression fixture 92, whereby the collet jaws 140 are forcibly urged inwardly about the longitudinal axis of the tubular collet 122 to frictionally engage the hypotube 22. The engagement of the O-ring 90 about the hypotube 22 also provides for additional securement by frictional engagement.

Figure 12:
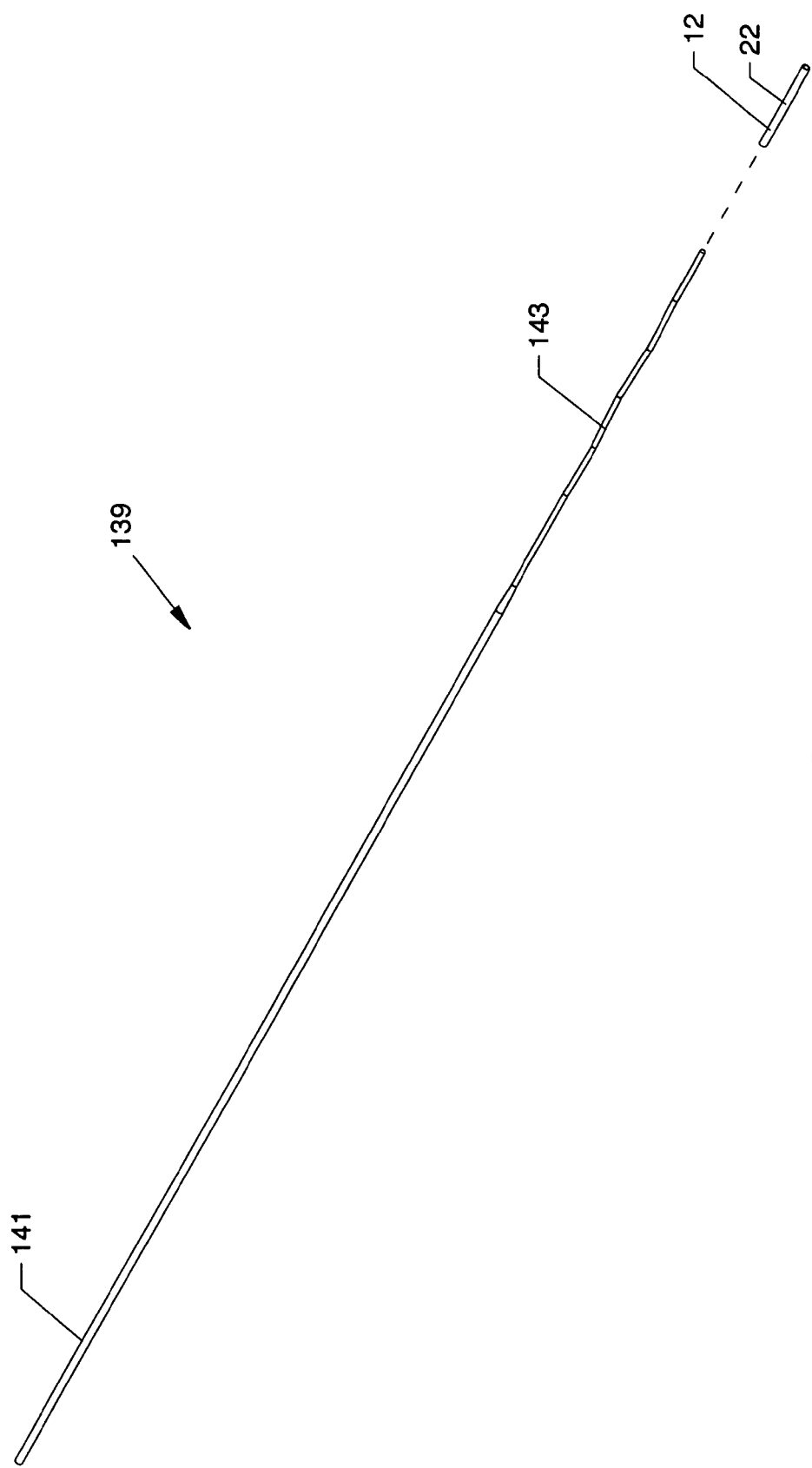
FIG. 12 illustrates an extension wire for use with the preferred nitinol wire infusion flow guidewire.
Figure 12A:
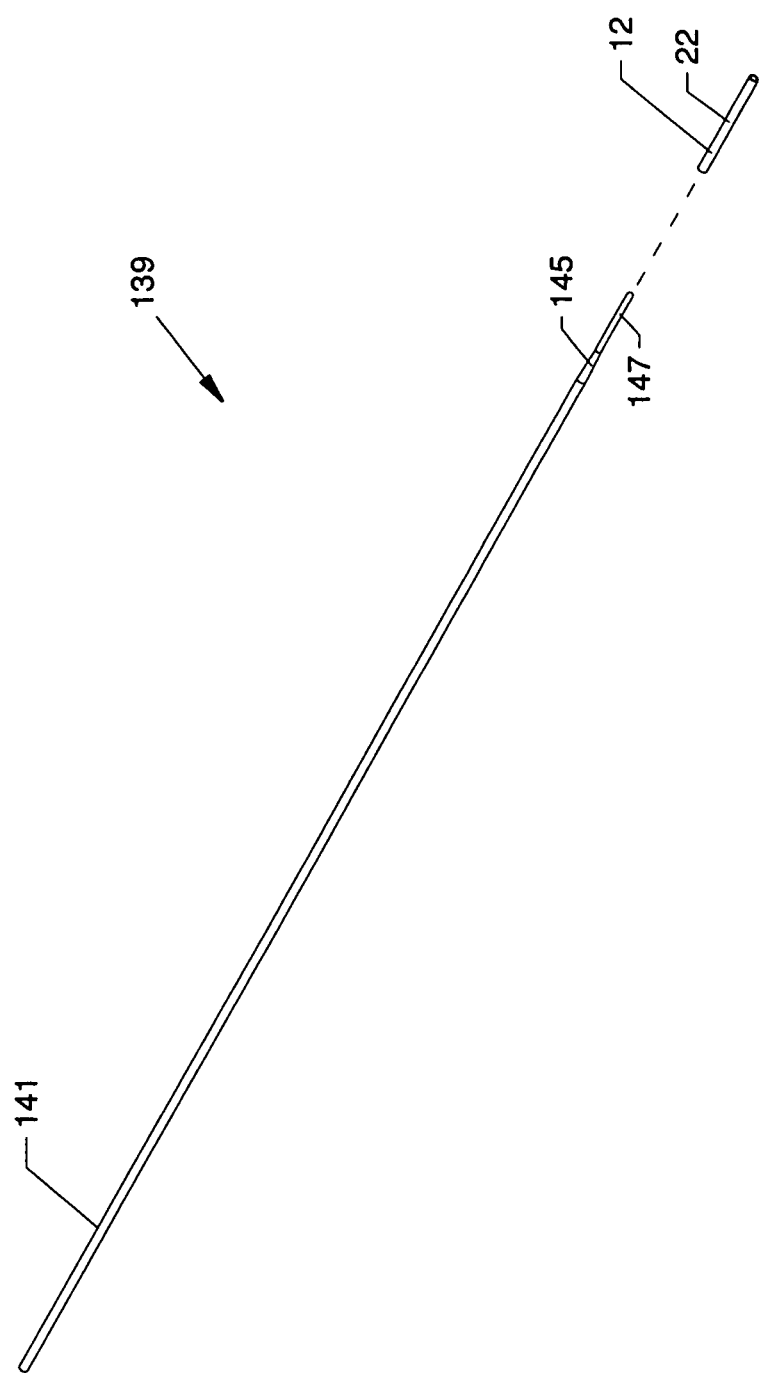
FIG. 12a is an isometric view of an alternate distal end shape for the extension wire of FIG. 12.

FIG. 12 illustrates a stainless steel extension wire 139 for use with the preferred all nitinol wire infusion flow guidewire 12, including a constant size body 141 and an irregular shaped distal end 143. The irregular shaped distal end 143 can be inserted into the inner diameter of the nitinol infusion flow guidewire 12 to be engaged therein in light frictional engagement to easily and quickly convert a rapid exchange length wire into an exchange length wire (for over-the-wire devices). As shown in FIG. 12a, another shape could be substituted for the irregular shaped distal end 143 including a tapered section 145 and a constant size extension 147 which can frictionally engage the inner diameter of the infusion flow guidewire 12.

Alternatively, other configurations of the present invention can be advantageous. First, an infusion flow guidewire can be fashioned where a proximal section of the nitinol hypotube 22 is replaced by a proximally located section of stainless steel hypotube joined to a shortened length of the nitinol tube, such as is used for the hypotube 22, instead of the full length nitinol hypotube 22. The drawn hypotube section 22a and components located distally thereto remain unchanged. In this construction, the proximal section of stainless steel structure provides a more pushable and torqueable proximal infusion flow guidewire end, thereby eliminating the need for and the use of the delivery sheath 16, as previously described. This approach requires a connection between the stainless steel hypotube section and the reduced length nitinol hypotube section, such as those seen in the 0.014 inch guard dog device (application Ser. No. 11/581,613) or 3 Fr swage proximal swage joint (application Ser. Nos. 11/702,990 and 11/702, 995). The proximal end of the nitinol section could be drawn down and inserted in the distal inner diameter of the stainless steel section and then swaging the stainless steel section over the drawn nitinol. Another configuration could be accomplished by drawing the distal end of the stainless steel, gold plating it, and then laser swaging the proximal end of the nitinol onto the distal stainless steel section. Such designs are more economically feasible due to the reduction in the use of nitinol.

A second alternative construction involves the jet orifices. The greatest difficulty is achieving a high velocity and significant flow rate for the jet orifices. However, if one were to produce a series of orifices, 8-10 orifices for example, along the distal end of the infusion flow guidewire 12, preferably on the collar 26, one could produce a weeping style infusion catheter similar to the Prostream guidewire. The orifices could be proximally, distally or perpendicularly directed in multiple combinations or arrangement thereof. In this case, the device would still have the advantage of a 0.014 inch profile versus the 0.035 inch profile for the Prostream, but would be incapable of conducting power pulse as previously described.

Thirdly, the connection for the pump to the infusion flow guidewire could be of an alternative arrangement. Rather than using a screw mechanism to squeeze the O-rings about the flow wire, one could use a hinged handle on a cam to advance a pusher plate to squeeze the O-rings.

Mode of Operation

This invention describes a 0.014 inch infusion flow guidewire system which can infuse fibrinolytics and which can also macerate and propel fluid or debris in a proximal direction. The guidewire system can be operated with devices using an AngioJet® system in various forms of implementation for treatment of thrombus in small vessels, such as in distal peripheral vessels, e.g., foot or other neurovascular sites. Delivery of the infusion flow guidewire 12, preferably of 0.014 inch diameter, is facilitated by inserting the delivery sheath 16 into and along the vasculature to position the distal end of the delivery sheath 16 at a location in close proximity to a thrombus site. Such positioning is facilitated by grasping the torque handle 18 and urging the delivery sheath 16 distally. Then, the flexible tip 24 of the infusion flow guidewire 12 can be inserted into and engage the proximal end of the torque handle 18, and thence, gain entry into the delivery sheath 16, whereby the hypotube 22 and the flexible tip 24 can be positioned distally therein by the use of the attached coupling assembly 14. In the alternative, the infusion flow guidewire 12 can be prepackaged in the delivery sheath 16 for unitary delivery. When delivery is accomplished, fibrinolytics can be introduced or maceration of thrombus can take place in conjunction with an AngioJet® system, such as disclosed in patent application Ser. No. 11/237,558 filed Sep. 28, 2005, entitled "Thrombectomy Catheter Deployment System," or with other AngioJet® systems. As previously described, the torque handle 18 can be tightened over and about the hypotube 22 and unitary longitudinal and rotary positioning of the infusion flow guidewire 12 including the hypotube 22 can be accomplished. The clamping action of the torque handle 18 can be terminated by loosening the collet nut 46, whereby the infusion flow guidewire 12 can be longitudinally and rotatingly positioned independently of the delivery sheath 16 by use of the attached coupling assembly 14 to achieve the desired position. When the infusion flow guidewire 12 is in the desired position, the coupling assembly 14 can be rotationally actuated to release the proximal end of hypotube 22 at the proximal end of the infusion flow guidewire 12 to allow separation of the hypotube 22 and the coupling assembly 14, thereby allowing access over and about the infusion flow guidewire 12 by other devices, as necessary.

Figure 14:
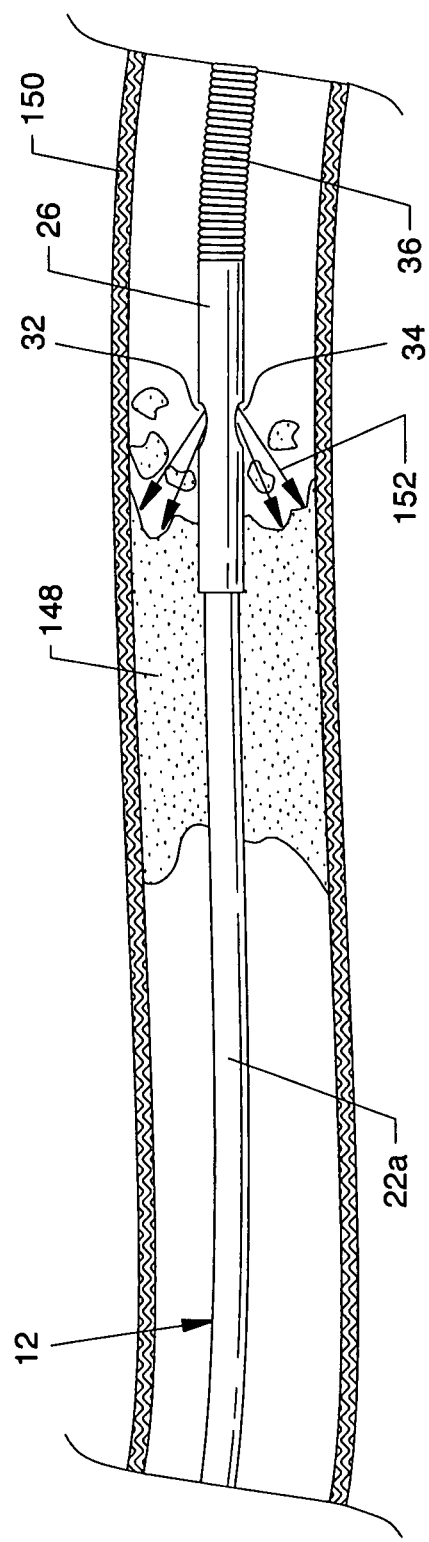
FIG. 14 shows the location of the jet orifices in close proximity to and distal to the thrombus; and, FIG. 15 shows the location of the jet orifices aligned within the thrombus.

FIGS. 13, 14 and 15 show various locations of the jet orifices 32 and 34 with respect to the thrombus 148 located in a vessel 150, such locations being used for various operating modes. FIG. 13 shows the location of the jet orifices 32 and 34 in close proximity to and proximal to the thrombus 148, FIG. 14 shows the location of the jet orifices 32 and 34 in close proximity to and distal to the thrombus 148, and FIG. 15 shows the location of the jet orifices 32 and 34 aligned within the thrombus 148.

Preferably, the invention is used with and is connected to an AngioJet® system. The invention may be used either to inject fibrinolytics, to macerate and propel fluid or debris in a proximal direction, or to accomplish all or other such functions. A hypothetical procedure, such as for use in the foot, for example, may be to advance the infusion flow guidewire to this very distal anatomy, farther than currently possible with available thrombectomy catheters. As shown in FIG. 13, fibrinolytics 146 can be delivered at a nominal rate, such as by use of an AngioJet® system, in close proximity to the proximal portion of a buildup of thrombus 148 located in the vessel 150 for the treatment and softening of the thrombus prior to thrombus removal.

As shown in FIG. 14, the jet orifices 32 and 34 can be positioned in close proximity and distal to the thrombus 148 where an AngioJet® system can deliver fibrinolytic at a nominal rate or in the power pulse mode, the latter mode of which proximally directs and infuses a fibrinolytic to the thrombus 152 of the thrombosed vessel segment in a direction as shown by arrows 152. This will ensure that the fibrinolytic is driven into the organized thrombus debris for effective loosening of the thrombus 148. Following a period of time, the physician would operate the same infusion flow guidewire 12 to macerate the organized debris by high pressure jet streams emanating proximally from the jet orifices 32 and 34 in a direction shown by arrows 152 The net effect of the procedure is that any thrombus 148 that would have been removed by a long duration drip is removed in the catheterization laboratory with the power pulse technique. This avoids the need to keep patients on a long term drip of fibrinolytics which is undesirable from a bleeding complication perspective. The flow rate and the jet orifice 32 and 34 arrangement of the infusion flow guidewire 12 result in a power direct infusion of fluid sufficient to disrupt and macerate the thrombus or push debris in the direction of the jet flow subsequent to breaking through the thrombus 148. Preferably, the infusion flow guidewire 12 is actuated in a to and fro motion, as well as a rotary motion.

As shown in FIG. 15, the jet orifices 32 and 34 are positioned in the midst of the thrombus 148. Again, an AngioJet® system can be used to deliver fibrinolytics under nominal pressure or under power pulse pressures. Such a location of the jet orifices 32 and 34 can be advantageous in treatment at the center of the thrombus 148 from the inside to the outside thereof. After a suitable length of time, high pressure jet streams emanating from the jet orifices 32 and 34 in a direction as shown by arrows 152 macerate the thrombus 148.

Preferably, the infusion flow guidewire 12 is actuated in a to and fro motion, as well as a rotary motion.

An aspiration catheter or an AngioJet® catheter, such as one with a proximal balloon, could be delivered over the infusion flow guidewire 12 and connected an AngioJet® system roller pump. Thus, the infusion flow guidewire system 10 could conduct thrombus maceration coupled with aspiration. Although the infusion flow guidewire system 10 may not be truly isovolumetric, there would be some aspiration of the material. Furthermore, the high velocity fluid jet stream from the infusion flow guidewire 12 is generally effective in macerating debris. Finally, once the debris is removed, there may need for other treatments. For example, a stent could be delivered over the same wire following the thrombectomy/lysis procedure. Other techniques for use of the infusion flow guidewire 12 would be to first treat the thrombus segment with the "Power Pulse" technique. Following this procedure, a pressurized bag of saline/lytic could be attached to the infusion flow guidewire 12 and the patient moved out of the catheterization laboratory.

Alternatively, the physician may elect to only conduct a drip type procedure with the infusion flow guidewire 12 or a nominal pressure slow infusion could be accomplished with an AngioJet® system. There are many potential treatment modalities. The AngioJet® system along with its capability of delivering fluid at pressures up to 20 kpsi, can enable the 0.014 inch infusion flow guidewire 12 to deliver a powerful stream of fluid sufficient to the treatment site, if required.

The entire infusion flow guidewire 12 is fashioned of nitinol to eliminate any flow restrictions between nitinol tubing and previously used stainless steel tube components and associated joint restrictions, as well as wall thickness strength constraints. The use of nitinol tubing also makes the infusion flow guidewire 12 kink resistant. The goal of the infusion flow guidewire system 10 is to enable delivery of as much a flow rate as possible to the jet orifices 32 and 34. The resulting flow rate, divided by the jet hole area, will yield the jet velocity. Vessel safety tests have shown that jet velocity higher than the AngioJet® catheter side exhaust holes (15 m/s) are safe, but that the velocities must be less than the AngioJet® internal jets (150 m/s). However, there may be occasions where destructive velocities in excess of 150 m/s may be required in treatment of calcific plaque, tissue destruction or disruption. Hence, the jet hole diameter and the entire flow resistance of the device is engineered to yield jet velocities in the range of 15 to 100 m/s. Aside from connections between stainless steel and nitinol, there may be other major restrictions that require attention. First, the infusion flow guidewire 12 should preferably be a rapid exchange length of 190 cm in order to achieve the least resistance as possible. Secondly, the ID of the nitinol infusion flow guidewire 12 should be as large as practical preferably 0.010 inch diameter dimension. Third, the drawn hypotube section 22a at the distal end of the infusion flow guidewire 12 is designed as short as possible in order to achieve an acceptably deliverable infusion flow guidewire. Importantly, an infusion flow guidewire 12 device of 0.014 inch can deliver a significant flow rate (>5 cc/min) to the jet orifices 32 and 34 using a typical AngioJet® pressure range of 0.25 kpsi to 12 kpsi.

Various modifications can be made to the present invention without departing from the apparent scope thereof.

PARTS LIST 10 infusion flow guidewire system
12 infusion flow guidewire
14 coupling assembly
16 delivery sheath
18 torque handle
20 high pressure supply line
22 hypotube
22a drawn hypotube section
24 flexible tip
26 reinforcement collar
28 laser weld
30 laser weld
32 jet orifice
32a-b holes
34 jet orifice
34a-b holes
36 flexible coil
38 core wire
38a core wire round section
38b core wire flat section
40 lumen
42 torque body
43a-c laser swags
44 collet
46 collet nut
48 strain relief
49 passage
50 bore
52 threads
54 annular tapered actuating surface
56 annular positioning ring
58 slots
60 jaws
62 tapered and arcuate surface
64 tapered and arcuate surface
66 tapered and arcuate surface
68 passageway
70 bore
72 bore
74 threads
76 tapered passage
78 passageway
80 annular tapered passageway
82 proximal knob
84 distal knob
85 threaded insert
86 set screws
88 threaded body
90 O-ring
92 compression fixture
94 bore
96 body hole
98 body hole
100 threads
102 threaded hole
104 threaded hole
106 threads
108 bore
109 annular end surface
110 tubular flange
112 passageway
114 passageway
116 annular recess
118 annular tapered actuating surface
120 threaded insert
122 tubular collet
124 bore
126 annular end surface
128 passageway
129 taper
130 bore
132 annular end surface
134 threads
136 passageway
138 distal wall
139 extension wire 140 jaws
141 constant size body
142 tapered and arcuate surface
143 irregular shaped distal end
144 passageway
145 tapered section
146 fibrinolytics
147 constant size body
148 thrombus
150 vessel
152 arrows It is claimed:

1. An infusion flow guidewire system comprising:
   a. an infusion flow guidewire having a proximal end, a distal end, at least one jet orifice, and a flexible tip at the distal end, wherein the flexible tip has a closed distal end and further comprises a coil and core wire:
   b. a delivery sheath having a proximally located torque handle, wherein the infusion flow guidewire is capable of passing through the delivery sheath; and
   c. a coupling assembly removeably attachable to the proximal end of the infusion flow guidewire to facilitate connection of the proximal end of the infusion flow guidewire to a pressurized fluid supply and to facilitate manipulation of the infusion flow guidewire,
wherein the torque handle of the delivery sheath includes proximal and distal ends and further includes:
   i. a torque body having a bore and external threads;
   ii. a collet for insertion into the bore of the torque body;
   iii. a collet nut for compressing the collet when tightened on the external threads; and
   iv. a strain relief having a passage carrying the proximal end of the delivery sheath, wherein the assembled torque handle provides coaxial accommodation of the delivery sheath and frictional engagement of the infusion flow guidewire when tightened, and wherein the infusion flow guidewire passes through the proximal and distal ends of the torque handle.

2. The infusion flow guidewire system of claim 1, wherein the delivery sheath has an outer diameter of 0.035 inch.

3. The infusion flow guidewire system of claim 1, wherein the delivery sheath has an inner diameter of 0.017 inch.

4. The infusion flow guidewire system of claim 1, wherein the delivery sheath is formed of polyimide.

5. The infusion flow guidewire system of claim 1, wherein the delivery sheath is formed of braided polyimide.

6. An infusion flow guidewire system comprising:
   a. an infusion flow guidewire having a proximal end, a distal end, at least one jet orifice, and a flexible tip at the distal end, wherein the flexible tip has a closed distal end and further comprises a coil and core wire;
   b. a delivery sheath having a proximally located torque handle, wherein the infusion flow guidewire is capable of passing through the delivery sheath; and
   c. a coupling assembly removeably attachable to the proximal end of the infusion flow guidewire to facilitate connection of the proximal end of the infusion flow guidewire to a pressurized fluid supply and to facilitate manipulation of the infusion flow guidewire,
wherein the coupling assembly includes:
   i. a generally stationary proximal knob and a rotatable distal knob, the proximal knob providing removable connection to a distal end of the pressurized fluid supply and the proximal knob providing removable attachment to the proximal end of the infusion flow guidewire;
   ii. a threaded insert;
   iii. a threaded body having an outside surface and a bore defining an inner diameter, the outside surface of the threaded body interacting with the threaded insert;
   iv. an O-ring having a diameter that is less than the inner diameter of the threaded body;
   v. a compression fixture; and
   vi. a tube collet,
wherein rotatably tightening the rotatable distal knob relative to the generally stationary proximal knob causes the threaded insert, the threaded body and the compression fixture to interact to compress the O-ring to seal about the proximal end of the infusion flow guidewire.

7. The infusion flow guidewire system of claim 6, wherein the delivery sheath has an outer diameter of 0.035 inch.

8. The infusion flow guidewire system of claim 6, wherein the delivery sheath has an inner diameter of 0.017 inch.

9. The infusion flow guidewire system of claim 6, wherein the delivery sheath is formed of polyimide.

10. The infusion flow guidewire system of claim 6, wherein the delivery sheath is formed of braided polyimide.

11. An infusion flow guidewire system comprising:
    a. an infusion flow guidewire having a proximal end, a distal end, at least one jet orifice, and a flexible tip at the distal end, wherein the flexible tip has a closed distal end and further comprises a coil and core wire;
    b. a delivery sheath having a proximally located torque handle, wherein the infusion flow guidewire is capable of passing through the delivery sheath; and
    c. a coupling assembly removeably attachable to the proximal end of the infusion flow guidewire to facilitate connection of the proximal end of the infusion flow guidewire to a pressurized fluid supply and to facilitate manipulation of the infusion flow guidewire,
wherein the torque handle of the delivery sheath includes proximal and distal ends and further includes:
    i. a torque body having a bore and external threads;
    ii. a collet for insertion into the bore of the torque body; and
    iii. a collet nut for compressing the collet when tightened on the external threads,
   wherein the assembled torque handle provides coaxial accommodation of the delivery sheath and frictional engagement of the infusion flow guidewire when tightened, and wherein the infusion flow guidewire passes through the proximal and distal ends of the torque handle.

12. The infusion flow guidewire system of claim 11, wherein the delivery sheath has an outer diameter of 0.035 inch.

13. The infusion flow guidewire system of claim 11, wherein the delivery sheath has an inner diameter of 0.017 inch.

14. The infusion flow guidewire system of claim 11, wherein the delivery sheath is formed of polyimide.

15. The infusion flow guidewire system of claim 11, wherein the delivery sheath is formed of braided polyimide.

16. A method of removing thrombus from vasculature, comprising:
    providing an infusion flow guidewire system comprising:
    a. an infusion flow guidewire having a proximal end, a distal end, at least one jet orifice, and a flexible tip at the distal end, wherein the flexible tip has a closed distal end and further comprises a coil and core wire;

b. a delivery sheath having a distal end and a proximally located torque handle, wherein the infusion flow guidewire is capable of passing through the delivery sheath; and c. a coupling assembly removeably attachable to the proximal end of the infusion flow guidewire to facilitate connection of the proximal end of the infusion flow guidewire to a pressurized fluid supply and to facilitate manipulation of the infusion flow guidewire, wherein the torque handle of the delivery sheath includes proximal and distal ends and further includes:

i. a torque body having a bore and external threads;

ii. a collet for insertion into the bore of the torque body; and iii. a collet nut for compressing the collet when tightened on the external threads, wherein the assembled torque handle provides coaxial accommodation of the delivery sheath and frictional engagement of the infusion flow guidewire when tightened, and wherein the infusion flow guidewire passes through the proximal and distal ends of the torque handle;

maneuvering the delivery sheath through the vasculature to position the distal end of the delivery sheath near a thrombus to be removed;

inserting the distal end of the infusion flow guidewire into the proximal end of the delivery sheath;

connecting the proximal end of the infusion flow guidewire to the pressurized fluid source; and positioning the at least one jet orifice of the infusion flow guidewire in the thrombus to be removed and expelling fluid from the at least one jet orifice to act upon the thrombus to remove thrombus by action of fluid expelled from the at least one jet orifice.

17. The method of claim 16, wherein inserting the infusion flow guidewire into the delivery sheath precedes maneuvering the delivery sheath through the vasculature to position the distal end of the delivery sheath near the thrombus to be removed.

18. The method of claim 16, wherein inserting the infusion flow guidewire into the delivery sheath follows maneuvering the delivery sheath through the vasculature to position the distal end of the delivery sheath near the thrombus to be removed.

19. The method of claim 16, further comprising:

removing the delivery sheath while leaving the infusion flow guidewire in the vasculature; and installing another device over the infusion flow guidewire.

20. The method of claim 19, wherein the another device is a stent.

21. The method of claim 19, wherein the another device is an aspiration catheter.

22. The method of claim 16, wherein connecting the proximal end of the infusion flow guidewire to the pressurized fluid source precedes inserting the distal end of the infusion flow guidewire into the proximal end of the delivery sheath.

23. The method of claim 16, wherein the pressurized fluid source is a high pressure source.

24. The method of claim 23, wherein the high pressure fluid source is capable of a pressure of up to about 20 kpsi.

25. The method of claim 23, wherein the high pressure fluid source is applied in pulses.

26. The method of claim 16, wherein positioning the at least one jet orifice of the infusion flow guidewire in the thrombus to be removed and expelling fluid from the at least one jet orifice to act upon the thrombus to remove thrombus by action of fluid expelled from the at least one jet orifice is accompanied by at least one additional actuation motion of the infusion flow guidewire.

27. The method of claim 26, wherein the at least one accompanying additional actuation motion is selected from the group consisting of to and fro motion and rotary motion.

28. The method of claim 16, wherein the expelled fluid includes fibrinolytic agents.

\* \* \* \* \*

UNITED STATES PATENT AND TRADEMARK OFFICE
CERTIFICATE OF CORRECTION

| | | |
|---|---|---|
| PATENT NO. | : 8,608,703 B2 | Page 1 of 1 |
| APPLICATION NO. | : 11/980164 | |
| DATED | : December 17, 2013 | |
| INVENTOR(S) | : Riles et al. | |

It is certified that error appears in the above-identified patent and that said Letters Patent is hereby corrected as shown below:

IN THE SPECIFICATION:
In Column 1, Line 31, delete "tortuousity" and insert -- tortuosity --, therefor.
In Column 2, Line 7, delete "interventionists" and insert -- interventionalists --, therefor.
In Column 7, Line 31, delete "section 22" and insert -- section 22a --, therefor.
In Column 8, Line 48, delete "section 22." and insert -- section 22a. --, therefor.
In Column 12, Lines 39-40, delete "thrombus 152" and insert -- thrombus 148 --, therefor.

IN THE CLAIMS:
In Column 15, Line 18, in Claim 1, delete "wire:" and insert -- wire; --, therefor.
In Column 16, Line 11, in Claim 6, delete "threaded body" and insert -- threaded body, --, therefor.

Signed and Sealed this
Fifteenth Day of April, 2014

Michelle K. Lee
*Deputy Director of the United States Patent and Trademark Office*